(12) United States Patent
Yamauchi et al.

(10) Patent No.: US 7,724,456 B2
(45) Date of Patent: May 25, 2010

(54) MULTIDIRECTIONAL SIMULTANEOUS OBSERVATION OPTICAL SYSTEM, IMAGE READING DEVICE, IMAGE READING METHOD, AND MULTIDIRECTIONAL SIMULTANEOUS OBSERVATION COMBINED OPTICAL SYSTEM

(75) Inventors: Kazuhide Yamauchi, Hirosaki (JP); Kiyoshi Toyamori, Aomori (JP); Takayoshi Shino, Toyohashi (JP); Toru Kato, Toyohashi (JP)

(73) Assignee: Technical Co., Ltd., Aomori (JP)

( * ) Notice: Subject to any disclaimer, the term of this patent is extended or adjusted under 35 U.S.C. 154(b) by 548 days.

(21) Appl. No.: 10/590,093

(22) PCT Filed: Dec. 27, 2004

(86) PCT No.: PCT/JP2004/019579

§ 371 (c)(1),
(2), (4) Date: May 4, 2007

(87) PCT Pub. No.: WO2005/083399

PCT Pub. Date: Sep. 9, 2005

(65) Prior Publication Data

US 2007/0279622 A1    Dec. 6, 2007

(30) Foreign Application Priority Data

Feb. 27, 2004    (JP)    ............................ 2004-054440
Sep. 22, 2004    (WO)    ................ PCT/JP2004/013849

(51) Int. Cl.
*G02B 5/04* (2006.01)
(52) U.S. Cl. .................................................... 359/834
(58) Field of Classification Search .......... 359/831–837
See application file for complete search history.

(56) References Cited

U.S. PATENT DOCUMENTS

2001/0055062 A1* 12/2001 Shioda et al. ................. 348/79

FOREIGN PATENT DOCUMENTS

| JP | 05-060538 | 3/1993 |
|----|-----------|--------|
| JP | 05-240607 | 9/1993 |
| JP | 05-322256 | 12/1993 |
| JP | 06-273339 | 9/1994 |
| JP | 08-076502 | 3/1996 |
| JP | 08-226902 | 9/1996 |
| JP | 2000-241363 | 9/2000 |
| JP | 2003-156333 | 5/2003 |

OTHER PUBLICATIONS

International Search Report corresponding to International Application No. PCT/JP2004/019579.

* cited by examiner

*Primary Examiner*—Euncha P Cherry
(74) *Attorney, Agent, or Firm*—Fay Sharpe LLP

(57) ABSTRACT

A multidirectional simultaneous observation optical system is composed of, as shown in FIG. 2, side image acquiring prism systems (145A, 145B) and so forth for acquiring side images of an object (11) and bottom image acquiring prism system (185F) for acquiring a bottom image. The prism system (145A) and so forth include optical path direction changing prisms (14A, 14B, 18F) and so forth respectively. An open space for acquiring the top image is defined directly above the object (11). The optical paths of the light beams emerging from the prism system (145A) and so forth extend upward from the object (11), and are so disposed as not to be blocked by the other prism systems. As a result, the object can be accurately observed from various directions simultaneously.

22 Claims, 24 Drawing Sheets

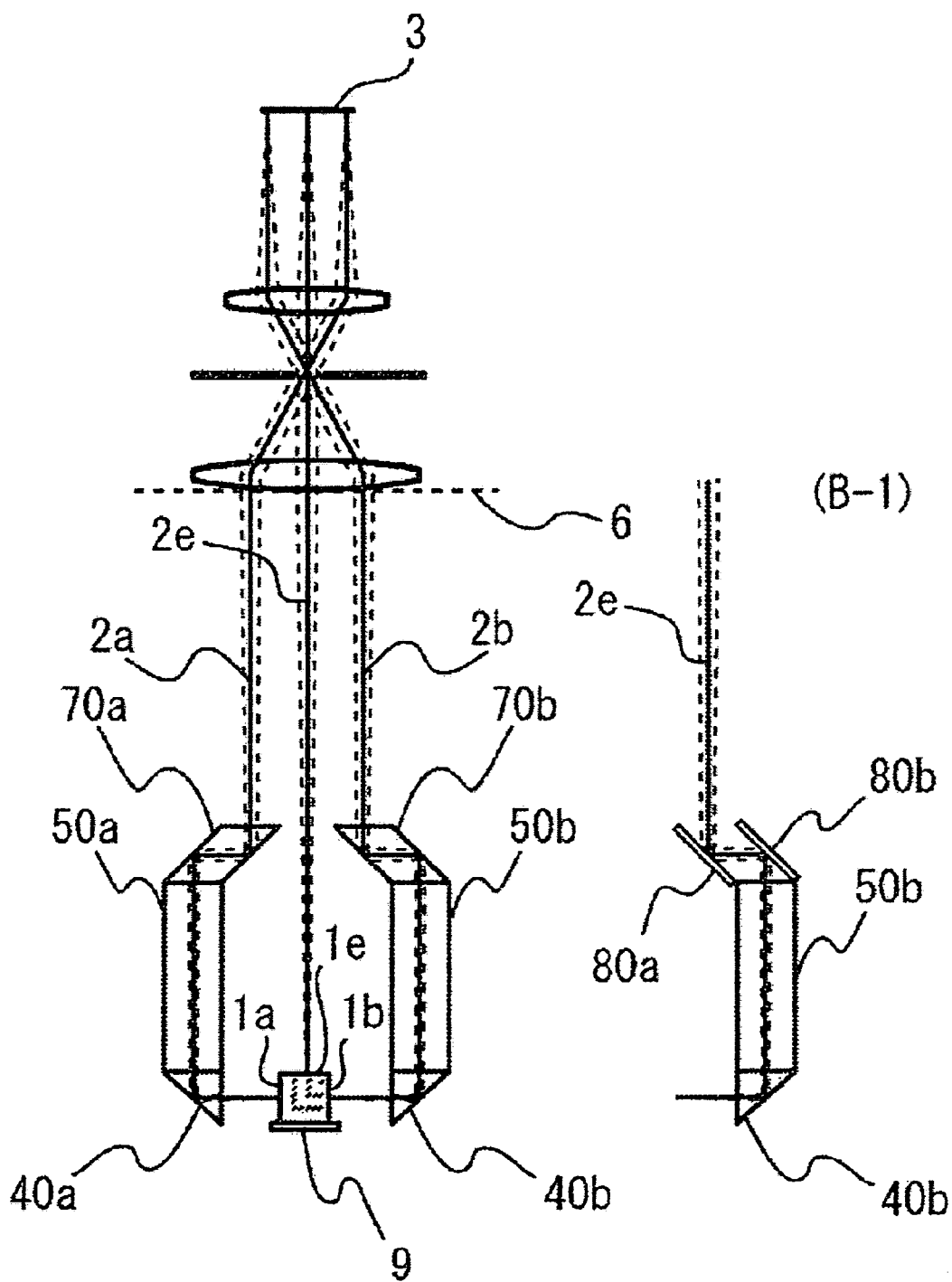

MULTIDIRECTIONAL SIMULTANEOUS OBSERVATION OPTICAL SYSTEM, IMAGE READING DEVICE, IMAGE READING METHOD, AND MULTIDIRECTIONAL SIMULTANEOUS OBSERVATION COMBINED OPTICAL SYSTEM

TECHNICAL FIELD

The present invention relates to a multidirectional simultaneous observation optical system, an image reading device, an image reading method and a multidirectional simultaneous observation combined optical system and, more particularly, to a multidirectional simultaneous observation optical system, an image reading device, an image reading method and a multidirectional simultaneous observation combined optical system capable of simultaneously observing an object to be inspected, in different directions with high accuracy, and improving the efficiency of inspection or the like.

BACKGROUND ART

The need sometimes arises for multidirectional observation and measurement of an appearance of an object to be inspected for the purpose of quality control or the like in various industrial fields.

FIG. 12 is a diagram showing an example of a conventional method of observing in many directions an object to be inspected. As shown in the figure, when an object to be inspected, having faces 1b, 1c, and 1e and other faces is observed, an external appearance of the object can be grasped by observation in directions toward the front, back, left, right, top and bottom faces, i.e., the six faces. In this example, the direction of observation of the object is changed by suitably moving a reading device 407, thus performing observation in many directions (directions toward the front, back, left, right, top and bottom faces). In the case where observation in many directions is performed by moving one reading device 407, a moving mechanism considerably complicated and highly sophisticated is required for positioning the reading device 407 and great effort and a long time are required for setting the reading device 407.

As an alternative to this method, a method has also been practiced in which an object to be inspected is observed in a direction freely selected and the direction of observation is changed by moving the object to be inspected. This method, however, requires considerable effort and a complicated process for moving and positioning the object to be inspected. Also, there are limits to the working efficiency and the improvement in observation accuracy.

To know the state of filing of applications for patent or the like aimed at simultaneous observation and measurement in many directions, a survey by search in Japan Patent Office Industrial Property Digital Library has been tried.

(I) Search survey 1
Menu: Publication text search
Search formula: (six faces+multiple faces)*measurement*simultaneous*(image+picture+figure+taking)
Data: Published patent application
Search date: Dec. 18, 2003
Number of hits: 28

(II) Search survey 2
Menu: Publication text search
Search formula: (six faces+multiple faces)*observation*simultaneous*(optical+prism)
Data: Published patent application, Examined patent application publication
Search date: Feb. 19, 2004
Number of hits: 4

In the results of these surveys, the one shown as patent document 1 below relates to a technique of grasping the positional relationship between a plurality of objects to be measured; the one shown as patent document 2 relates to use of an arrangement based on a plurality of mirrors for shape measurement in a case where a dead angle occurs (these are the results of search survey 1); and the one shown as patent document 3 relates to a technique for improving the resolution of an optical distance sensor and reducing the secondary light reflection sensitivity of the sensor.

Patent Document 1: Japanese Patent Laid-Open No. 2003-156333, "Distance measuring apparatus and others", Abstract.
Patent Document 2: Japanese Patent Laid-Open No. 5-322526, "Three dimensional shape measuring apparatus", Abstract.
Patent Document 3: Japanese Patent Laid-Open No. 5-240607, "Optical distance sensor", Abstract.

DISCLOSURE OF THE INVENTION

Problems to be Solved by the Invention

The example of the conventional art described above with reference to FIG. 12 also comprises an arrangement in which a necessary number of reading devices 407 are disposed at fixed positions for observation in different directions to reduce the time required for observation and measurement in many directions of an object to be inspected. This method is effective in saving time but increases the cost.

FIG. 13 is a diagram showing the relationship between a face 401 of an object to be inspected, a lens 405 and an image plane 403. The distance from a lens 405 end position 406 to the surface 401 of the object to be inspected, as shown in FIG. 13, is called a working distance (hereinafter referred to as WD) 402. In ordinary cases, the WD of a lens of fixed power is not changed. If the imaging positional relationship shown in the figure is not satisfied, a defocus from the in-focus plane occurs and a sharp image cannot be output from the image reading device.

FIG. 14 is a diagram showing the arrangement of components of a system in which the components are arranged to observe in many directions an object to be inspected (a cube in the figure) while the number of reading devices is reduced to reduce the cost. In this method, as shown in the figure, plane mirrors 4030a to 4030f are used and the relationship between the plane mirrors in placement relative to each other is adjusted so that light for images of six faces of the object to be inspected 1a to 1f is directed to a lens 405. The WDs to these faces have three values different from each other: (1) a common value representing values 2a to 2d equal to each other, (2) a value 2e, and (3) a value 2f. This method allows the occurrence of a difference between the WDs and, hence, defocusing from the in-focus plane, and the reading device is not capable of simultaneously and accurately observing the six faces of the object to be inspected.

A case in which observation is performed with the human eye with which the observation system is replaced will be considered. Since the human eye can automatically focus with respect to the WD having the three values, the drawback with the reading device is reduced to some extent in six-directional simultaneous observation of the object to be inspected. However, a time and action for moving the line of sight are required and observation requires an increased effort and time, which cause fatigue. As a result, the observation accuracy is reduced in a shorter time period.

It is, therefore, an object of the present invention to provide, as a solution to the above-described problems of the conventional art, a multidirectional simultaneous observation optical system, an image reading device, an image reading method and a multidirectional simultaneous observation combined optical system capable of simultaneously observing an object to be inspected, in different directions with high accuracy, and improving the efficiency of inspection or the like.

Means for Solving the Problems

The inventor of the present invention made studies about the above-described problems, found that the problems can be solved by using a prism placement method for providing one WD for images from different faces, and achieved the present invention as a result of this finding. That is, the invention claimed or at least disclosed in the present application as means for solving the above-described problems is as described below.

(1) A multidirectional simultaneous observation optical system having at least one of one, two or more side face imaging prism systems for obtaining side face images of one, two or more side faces of an object to be inspected and a bottom face imaging prism system for obtaining a bottom face image, the optical system being characterized in that each of the side face imaging prism systems has an optical path direction changing prism or an optical path direction changing prism function; the prism systems are provided by the side of an open space for obtaining an image of the top face of the object to be inspected so that the open space is secured right above the object to be inspected, and so that an object mount space portion is secured; and the prism systems are placed so that the optical paths for light exiting the prism systems extend upward above the object to be inspected, or along the same direction in parallel with each other, and so that the optical path is not obstructed.

(2) A multidirectional simultaneous observation optical system including one, two or more side face imaging prism systems for obtaining side face images of one, two or more side faces of an object to be inspected and a bottom face imaging prism system for obtaining a bottom face image, the optical system being characterized in that each of the side face imaging prism systems and the bottom face imaging prism system has an optical path direction changing prism or an optical path direction changing prism function; the prism systems are provided so as to occupy side spaces around an open space for obtaining an image of the top face of the object to be inspected and a space below the open space such that the open space is secured right above the object to be inspected, and such that an object mount space portion is secured; and the prism systems are placed so that the optical paths for light exiting the prism systems extend upward above the object to be inspected, or along the same direction in parallel with each other, and so that the optical path from each prism system is not obstructed by any of the other prism systems.

(3) The multidirectional simultaneous observation optical system described in (1) or (2), characterized in that each of the side face imaging prism systems and the bottom face imaging prism system is provided with an optical path length correcting prism or an optical path length correcting prism function above the optical path direction changing prism or the optical path direction changing prism function, the optical path length correcting prism or the optical path length correcting prism function being provided for the purpose of equalizing the working distance of the faces of the object to be inspected other than the top face of the same to the working distance of the top face.

(4) The multidirectional simultaneous observation optical system described in (3), characterized in that the optical path length correcting prism or the optical path length correcting prism function is formed so as to be interchangeable or optical path length adjustable in order to make optical path length correction according to the shape and size of the object to be inspected.

(5) The multidirectional simultaneous observation optical system described in (3) or (4), characterized in that a 45° mirror prism or a prism having a 45° mirror prism function is used as the optical path direction changing prism or the optical path direction changing prism function in the side face imaging prism system, and a trapezoidal prism or a triangular prism capable of changing the direction two times or a prism having the corresponding function is used as the optical path direction changing prism or the optical path direction changing prism function in the bottom face imaging prism system.

(6) The multidirectional simultaneous observation optical system described in any one of (3) to (5), characterized in that a penta prism capable of obtaining an erect image or a prism having the corresponding function is used as the optical path direction changing prism or the optical path direction changing prism function in the side face imaging prism system.

(7) The multidirectional simultaneous observation optical system described in any one of (1) to (6), characterized in that an optical path shifting prism or an optical path shifting prism function for shifting the optical path is provided above the optical path direction changing prism in each prism system.

(8) The multidirectional simultaneous observation optical system described in (7), characterized in that the optical path shifting prism or the optical path shifting prism function is formed so as to reduce the optical path section for optical output from the corresponding face of the object to be inspected, in order to improve the resolution by reducing the area of light incident on a lens or the like.

(9) The multidirectional simultaneous observation optical system described in any one of (3) to (8), characterized by having object carrying means on which two or more objects to be inspected are mounted and which can carry and move the objects to be inspected via the object mount space portion, and characterized in that each prism system is placed so that a path for the object carrying means is secured.

(10) The multidirectional simultaneous observation optical system described in any one of (3) to (9), characterized in that the four side face imaging prism systems are provided and image information on the object to be inspected can be obtained as light in six directions including the direction from the top face from which an optical output can be obtained without each prism system.

(11) The multidirectional simultaneous observation optical system described in (10), characterized in that two pairs of side face imaging prism systems opposed to each other with the object mount space portion interposed therebetween are placed as the four side face imaging prism systems orthogonally to each other or at any angle from each other.

(12) The multidirectional simultaneous observation optical system described in any one of (3) to (10), characterized by further including a lens facing along the optical output direction of the side face imaging prism system and the bottom face imaging prism system or a telecentric lens capable of forming a telecentric system on the side of the object to be inspected.

(13) The multidirectional simultaneous observation optical system described in (12), characterized in that the lens has a depth of field sufficient for simultaneously adjusting in-focus planes for the faces even with respect to a complicated object to be inspected having a spherical or hyper-polyhedral shape or the like.

(14) An image reading device characterized by having the multidirectional simultaneous observation optical system described in any one of (11) to (13) and an electronic image pickup device including a CCD, a CMOS or a line CCD for performing photoelectric conversion processing on light obtained through the lens, and characterized in that the image reading device can be used for image analysis including image measurement.

(15) An image reading method characterized by obtaining image information in the form of light on the faces of an object to be inspected by means of the multidirectional simultaneous observation optical system described in any one of (11) to (13), obtaining electrically processible image information by performing photoelectric conversion processing on light obtained through the lens, by means of an electronic image pickup device including a CCD, a CMOS or a line CCD, and using the image information for image analysis including image measurement.

(16) The multidirectional simultaneous observation optical system described in (1) or (2), characterized in that the open space is formed above the optical path direction changing prism or the optical path direction changing prism function in each of the side face imaging prism system and the bottom face imaging prism system to enable visual observation with the human eye to be easily performed.

(17) The multidirectional simultaneous observation optical system described in (16), characterized in that a triangular mirror prism or a prism having a triangular mirror prism function is used as the optical path direction changing prism or the optical path direction changing prism function in the side face imaging prism system, and a trapezoidal prism or a triangular prism capable of changing the direction two times or a prism having the corresponding function is used as the optical path direction changing prism or the optical path direction changing prism function in the bottom face imaging prism system.

(18) The multidirectional simultaneous observation optical system described in (16) or (17), characterized in that a pentagonal prism capable of obtaining an erect image or a prism having the corresponding function is used as the optical path direction changing prism or the optical path direction changing prism function in the side face imaging prism system.

(19) The multidirectional simultaneous observation optical system described in any one of (16) to (18), characterized in that an antireflection prism or an antireflection prism function is provided above the trapezoidal prism, the triangular prism or the corresponding function.

(20) The multidirectional simultaneous observation optical system according to any one of (16) to (19), characterized by having object carrying means on which two or more objects to be inspected are mounted and which can carry and move the objects to be inspected via the object mount space portion, and characterized in that each prism system is placed so that a path for the object carrying means is secured.

(21) The multidirectional simultaneous observation optical system described in any one of (16) to (20), characterized in that the four side face imaging prism systems are provided and image information on the object to be inspected can be obtained as light in six directions including the direction from the top face from which an optical output can be obtained without the prism system.

(22) The multidirectional simultaneous observation optical system described in (21), characterized in that two pairs of side face imaging prism systems opposed to each other with the object mount space portion interposed therebetween are placed as the four side face imaging prism systems orthogonally to each other or at any angle from each other.

(23) A multidirectional simultaneous observation combined optical system characterized by using the two or more multidirectional simultaneous observation optical systems described in (1) or (2), and characterized in that multidirectional simultaneous observation of an object to be inspected can be performed by means of the multidirectional simultaneous observation optical systems.

ADVANTAGES OF THE INVENTION

The multidirectional simultaneous observation optical system, the image reading device, the image reading method and the multidirectional simultaneous observation combined optical system of the present invention are arranged as described above to enable the faces of an object to be inspected to be simultaneously observed with accuracy and to improve the efficiency of inspection or the like.

A further detailed description will be made. The effects described below can be obtained by using the multidirectional simultaneous observation optical system, the image reading device, the image reading method or the multidirectional simultaneous observation combined optical system of the present invention.

(I) The in-focus planes can be simultaneously adjusted in all the six-face directions irrespective of whether the shape of the object to be inspected can be generally grasped as a cubic shape or the shape of rectangular block; images can be simultaneously provided without any eclipse; image analysis for external defect inspection or the like can be performed with accuracy; the time required for inspection or the like can be reduced; the efficiency of inspection or the like can be improved; and the cost can be reduced (the multidirectional simultaneous observation optical system, the image reading device, the image reading method and the multidirectional simultaneous observation combined optical system, as described above in (1), (4), (12), (14) and (16) for example).

(II) Even in a case where the object to be inspected is a polyhedral body having seven or more faces including upper and lower faces, the number of sets of side face imaging prism systems is increased to ensure that the in-focus planes are simultaneously adjusted for all the faces, and that images can be simultaneously provided without any eclipse (the multidirectional simultaneous observation optical system, the image reading device, the image reading method and the multidirectional simultaneous observation combined optical system, as described above in (4) for example).

(III) Even in a case where the object to be inspected is a spherical or hyper-polyhedral body, the depth of field of the lens of the reading device is increased to ensure that the in-focus planes can be adjusted, and that images can be simultaneously provided without any eclipse (the multidirectional simultaneous observation optical system, the image reading device, the image reading method and the multidirectional simultaneous observation combined optical system, as described above in (4) for example).

(IV) The 45° mirror prism in the side face imaging prism system is replaced with a penta prism or the triangular mirror prism is replaced with a pentagonal prism to enable erect images to be simultaneously provided (the multidirectional simultaneous observation optical system, the image reading device, the image reading method and the multidirectional simultaneous observation combined optical system, as described above in (6) and (8) for example).

(V) An additional component for an optical path shifting prism function, such as an optical path shifting prism or optical path shifting plane mirrors, is provided to reduce the area of light incident on the lens. The size per pixel of the object image taken by the image pickup device is thereby reduced to improve the resolution (the multidirectional simultaneous observation optical system, the image reading device, the image reading method and the multidirectional simultaneous observation combined optical system, as described above in (7) and (8) for example).

(VI) A carriage path through which objects to be inspected can be moved is provided to enable multidirectional simultaneous observation of a multiplicity of objects to be inspected to be continuously performed (the multidirectional simultaneous observation optical system, the image reading device, the image reading method and the multidirectional simultaneous observation combined optical system, as described above in (9) for example).

(VII) A telecentric lens for forming a telecentric system on the side of the object to be inspected is used as the lens of the reading device. From the characteristics of the telecentric lens, the size of the prisms can be reduced; the prisms can be placed closer to each other; the overall size can be reduced; and image measurement such as size defect inspection can be performed with accuracy (the multidirectional simultaneous observation optical system, the image reading device, the image reading method and the multidirectional simultaneous observation combined optical system, as described above in (2) and (12) for example).

BRIEF DESCRIPTION OF THE DRAWINGS

FIG. 2-2 is an explanatory diagram showing an example of arrangement of an observation optical system specific for obtaining a bottom face image in the multidirectional simultaneous observation optical system of the present invention;

FIG. 2-3 is a perspective view showing the example of arrangement of the observation optical system specific for obtaining a bottom face image, shown in FIG. 2-2;

FIG. 2-4 is a perspective view showing the example of arrangement of the observation optical system specific for obtaining a bottom face image, shown in FIG. 2-2;

FIG. 2-5 is a perspective view showing the example of arrangement of the observation optical system specific for obtaining a bottom face image, shown in FIG. 2-2;

FIG. 2-6 is a perspective view showing the example of arrangement of the observation optical system specific for obtaining a bottom face image, shown in FIG. 2-2;

FIG. 2-7 is a perspective view showing the example of arrangement of the observation optical system specific for obtaining a bottom face image, shown in FIG. 2-2;

FIG. 3 is a perspective view showing an arrangement for obtaining image information on six faces as an example of arrangement of the multidirectional simultaneous observation optical system of the present invention;

FIG. 5 is a perspective view showing an example of a basic arrangement of a multidirectional simultaneous observation optical system of the present invention for obtaining erect images;

FIG. 6(B) is a longitudinal sectional view of a multidirectional simultaneous observation optical system of the present invention to which another arrangement is added to that in FIG. 6(A), FIG. 6(B) being an explanatory diagram showing a situation in which imaging is achieved, (B-1) being a longitudinal sectional view of still another multidirectional simultaneous observation optical system of the present invention;

FIG. 6-2 is a plan view showing an example of placement of the multidirectional simultaneous observation optical system of the present invention;

FIG. 7 is an explanatory diagram showing a principle-arrangement of an image reading device of the present invention, (A) mainly showing side face imaging prism systems, (B) mainly showing side face imaging prism systems;

Figure 1:
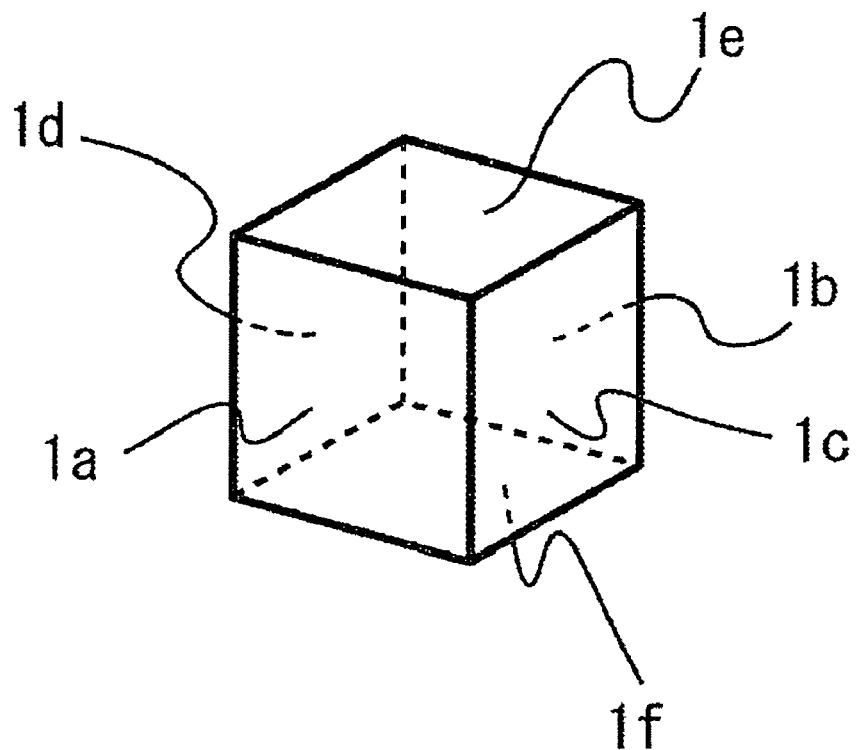
FIG. 1 is a perspective explanatory diagram showing a model for an object to be inspected, used for the description of the present invention.

DESCRIPTION OF SYMBOLS 1a to 1f . . . Faces of object to be inspected, 10 . . . Human eye, 11 . . . Object to be inspected, 14A, 14B, 18F . . . Optical path direction changing prism, 15A, 15B, 15F . . . Optical path length correcting prism, 145A, 145B . . . Side face imaging prism system, 185F . . . Bottom face imaging prism system, 19 . . . Portion on which object to be inspected is mounted (object carrying means, object mount portion), 2a, 2b, 2e, 2f . . . WD, 213 . . . Electronic image pickup device such as CCD or CMOS, 2145A, 2145B, 2145C . . . Side face imaging prism system, 215 . . . Lens, 218 . . . Trapezoidal prism, 2185F . . . Bottom face imaging prism system, 3 . . . Image plane on which object is imaged 40a, 40b, 40c, 40d . . . 45° mirror prism, 41a to 41d . . . Optical path direction changing prism (triangular prism)

5 . . . Lens, 50a to 50f . . . Optical path length correcting prism

6 . . . Lens end surface, 60a to 60d . . . Penta prism, 61a to 61d . . . Pentagonal prism 70a, 70b . . . Optical path shifting prism 8a, 8b . . . Trapezoidal prism, 80a, 80b . . . Optical path shifting plane mirror 9 . . . Object carrying means (object mount portion), 90 . . . Antireflection prism A-A, A-A', B-B . . . Cutting line for explanation 401 . . . Face of object to be inspected, 402 . . . Working distance (WD), 402a to 402f . . . WD, 403 . . . Image plane, 4030a to 4030f . . . Plane mirror, 404 . . . Image pickup device, 405 . . . Lens, 406 . . . Lens end position, 407 . . . Reading device 35 . . . Optical path length correcting prism in observation optical system specific for obtaining bottom face image 38F . . . Optical path direction changing prism (portion) in observation optical system specific for obtaining bottom face image 39 . . . Portion on which object to be inspected is mounted (object mount portion)

P1, P2, P3, P4, P5, P6, P7, P8 . . . Side face imaging prism system

BEST MODE FOR CARRYING OUT THE INVENTION

The present invention will be described below in detail with reference to the drawings. In some cases in the following description, elements having basically the same functions and beams of light exiting from corresponding prism surfaces are indicated by the same reference characters.

FIG. 1 is a perspective explanatory diagram showing a model for an object to be inspected, used for the description of the present invention.

Figure 2:
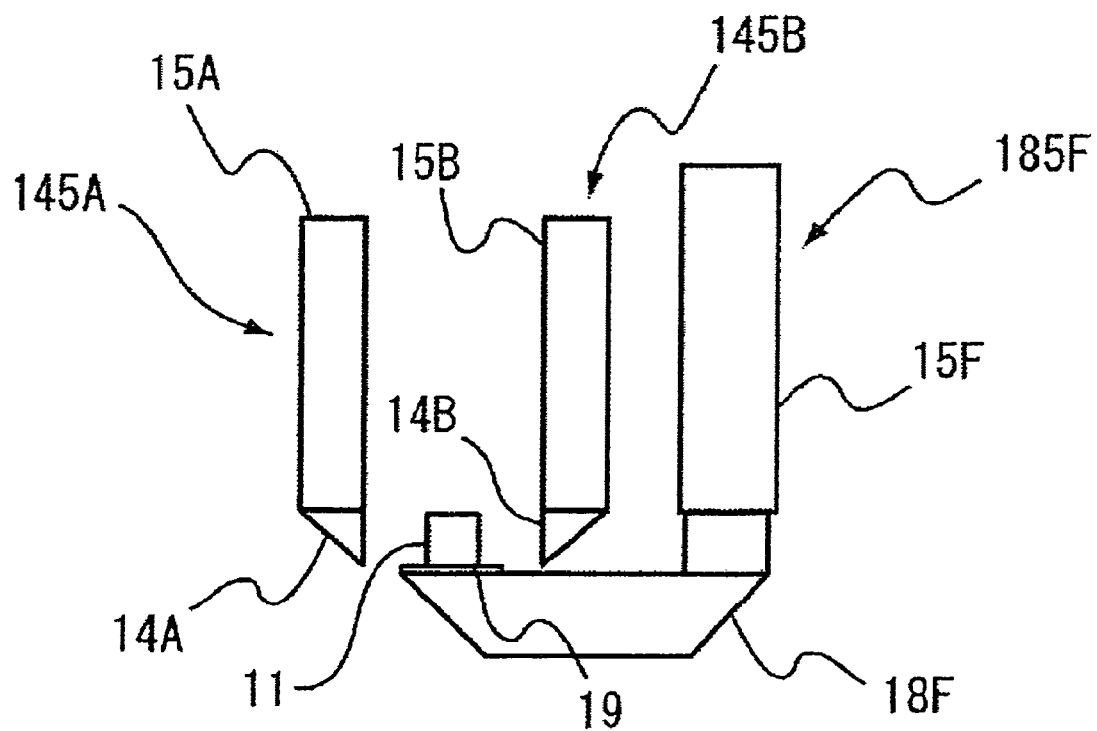
FIG. 2 is an explanatory diagram schematically showing a basic arrangement of a multidirectional simultaneous observation optical system in accordance with the present invention.
Figure 2:
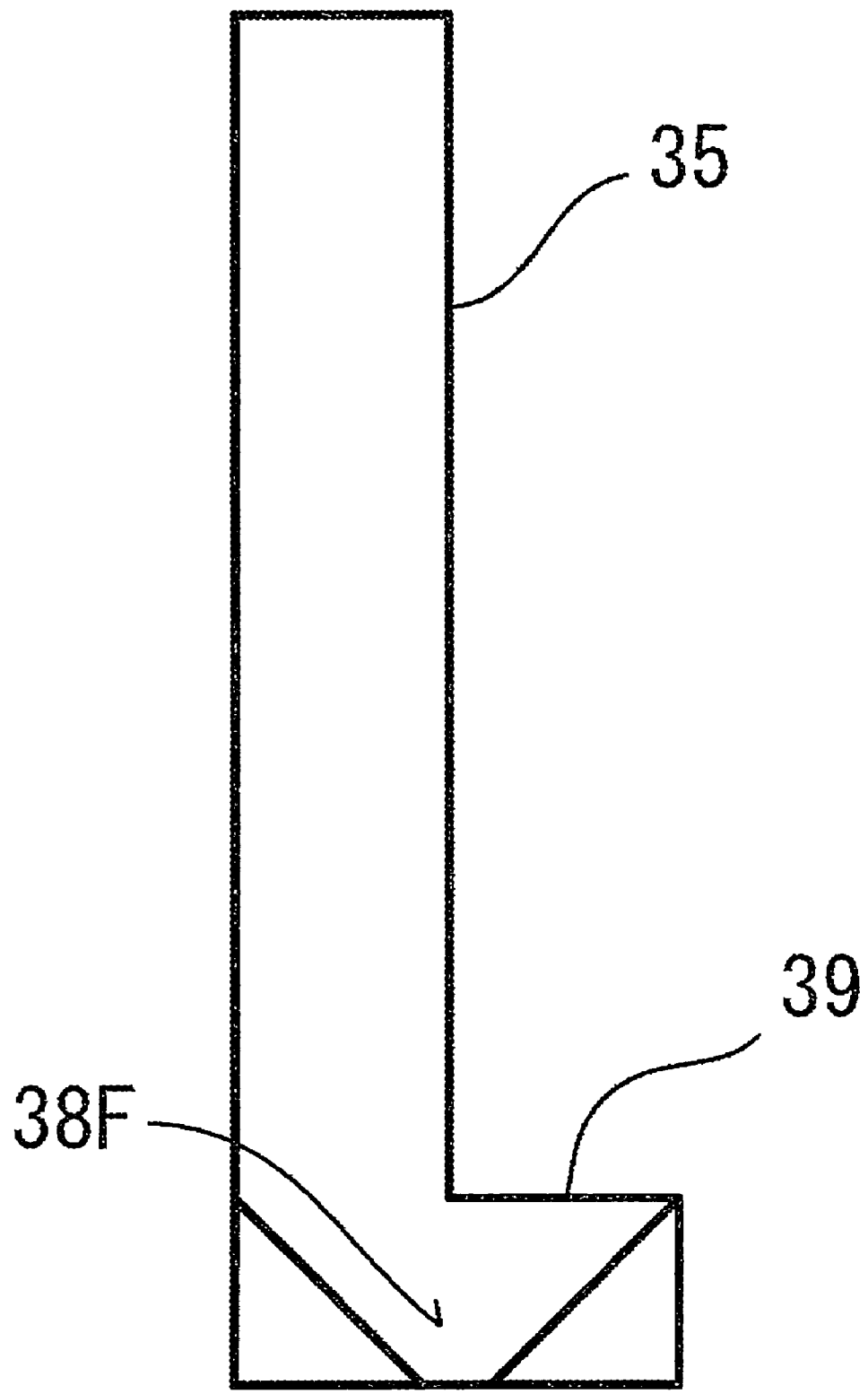

FIG. 2 is an explanatory diagram schematically showing a basic arrangement of a multidirectional simultaneous observation optical system in accordance with the present invention.

Referring to FIG. 2, the multidirectional simultaneous observation optical system is an optical system including one, two or more side face imaging prism systems 145A and 145B for obtaining side face images of one, two or more side faces of an object 11 to be inspected, and a bottom face imaging prism system 185F for obtaining a bottom face image. The side face imaging prism system 145A and so on and the bottom face imaging prism system 185F respectively have optical path direction changing prisms 14A, 14B, 18F, and so on or an optical path direction changing prism function (hereinafter referred to collectively as "optical path direction changing prism", occasionally). An essential arrangement is provided in which the prism systems 145A, 185F, and so on are placed so as to occupy side spaces around an open space for obtaining an image of the top face of the object 11 to be inspected and a space below the open space such that the open space is secured right above the object 11 to be inspected, and such that a space portion for mounting the object 11 to be inspected is secured, and so as to ensure that each of the optical paths from the prism systems 145A, 185F, and so on, through which light exiting from the corresponding prism system travels, extends upward above the object 11 to be inspected, without being obstructed by any of the other prism systems.

Reference numerals 19 in FIG. 2 denote a portion on which the object to be inspected is mounted. As this portion, an object carrying means may be provided, as described below.

In the multidirectional simultaneous observation optical system thus arranged, side face images of one, two or more side faces of the object 11 to be inspected are obtained by one, two or more side face imaging prism systems 145A, 145B, and so on and a bottom face image is obtained by the bottom face imaging prism system 185F.

The directions of the optical path through which light exits from the object 11 to be inspected and enters the optical path direction changing prism 14A and so on of the side face imaging prism system 145A and so on and the bottom face imaging prism system 185F are changed by the optical path direction changing prism 14A and so on so as to extend upward above the object 11 to be inspected. A top face image of the object 11 to be inspected is obtained through the open space secured right above the object, i.e., without being specially passed through a prism system.

The prisms systems 145A, 185F, and so on occupy the side spaces around the open space or the space below the open space, so that the space portion for mounting the object 11 to be inspected is secured.

The provision and arrangement of the prism systems 145A, 185F, and so on ensure that each of the optical paths from the prism systems 145A, 185F, and so on, through which light exiting from the corresponding prism system travels, extends upward above the object 11 to be inspected, without being obstructed by any of the other prism systems. The light traveling through the prism system is obtained as the image of the corresponding face.

Referring to FIG. 2, the prism systems 145A, 185F, and so on can be placed so that the optical paths for light exiting therefrom extend along the same direction parallel to each other, and so that the optical path from one prism system is not obstructed by any of the other prism systems.

If the components are arranged as described above, principal rays passing through centers of apertures in the optical system are parallel to each other on the inspection object side of a lens. In the multidirectional simultaneous observation optical system of the present invention, therefore, a telecentric optical system with no change in power with respect to the distance to the object to be inspected is realized. Therefore no change in power occurs due to a focusing error. Further, no visual difference with respect to the object to be inspected occurs between central and peripheral portions of each image, so that no sense of distinction between far and near conditions through the entire visual field; images can be obtained without distortion; and a high degree of accuracy can be obtained in image processing and measurement.

Referring to the figure, the above-described side face imaging prism system 145A and so on and the bottom face imaging prism system 185F in the multidirectional simultaneous observation optical system of the present invention are respectively provided with optical path length correcting prisms 15A, 15B, 15F, and so on or an optical path length correcting prism function (hereinafter also referred to collectively as "optical path length correcting prism") above the optical path direction changing prism 14A and so on in addition to the above-described arrangement. The optical path length correcting prisms 15A, 15B, 15F, and so on are provided for the purpose of equalizing the WDs of the faces of the object 11 to be inspected other than the top face of the same to the WD of the top face.

This arrangement ensures that in the multidirectional simultaneous observation optical system of the present invention the WDs of the faces other than the top face of the object 11 to be inspected are corrected by the optical path length correcting prisms 15A, 15B, 15F, and so on so as to be equal to the WD of the top face. That is, the WDs are equalized by this correction with respect to the images from the faces to adjust the in-focus plane, thereby enabling a reading device to output sharp images.

The optical path length correcting prisms 15A, 15B, 15F, and so on may be changed as desired to enable optical path length correction according to the shape and size of the object to be inspected. An arrangement for forming optical paths so that the optical path lengths can be adjusted by using some other suitable means may alternatively be adopted.

FIG. 2-2 is an explanatory diagram, i.e., a side view, showing an example of arrangement of an observation optical system specific for obtaining a bottom face image in the multidirectional simultaneous observation optical system of the present invention.

Figures 2, 3:
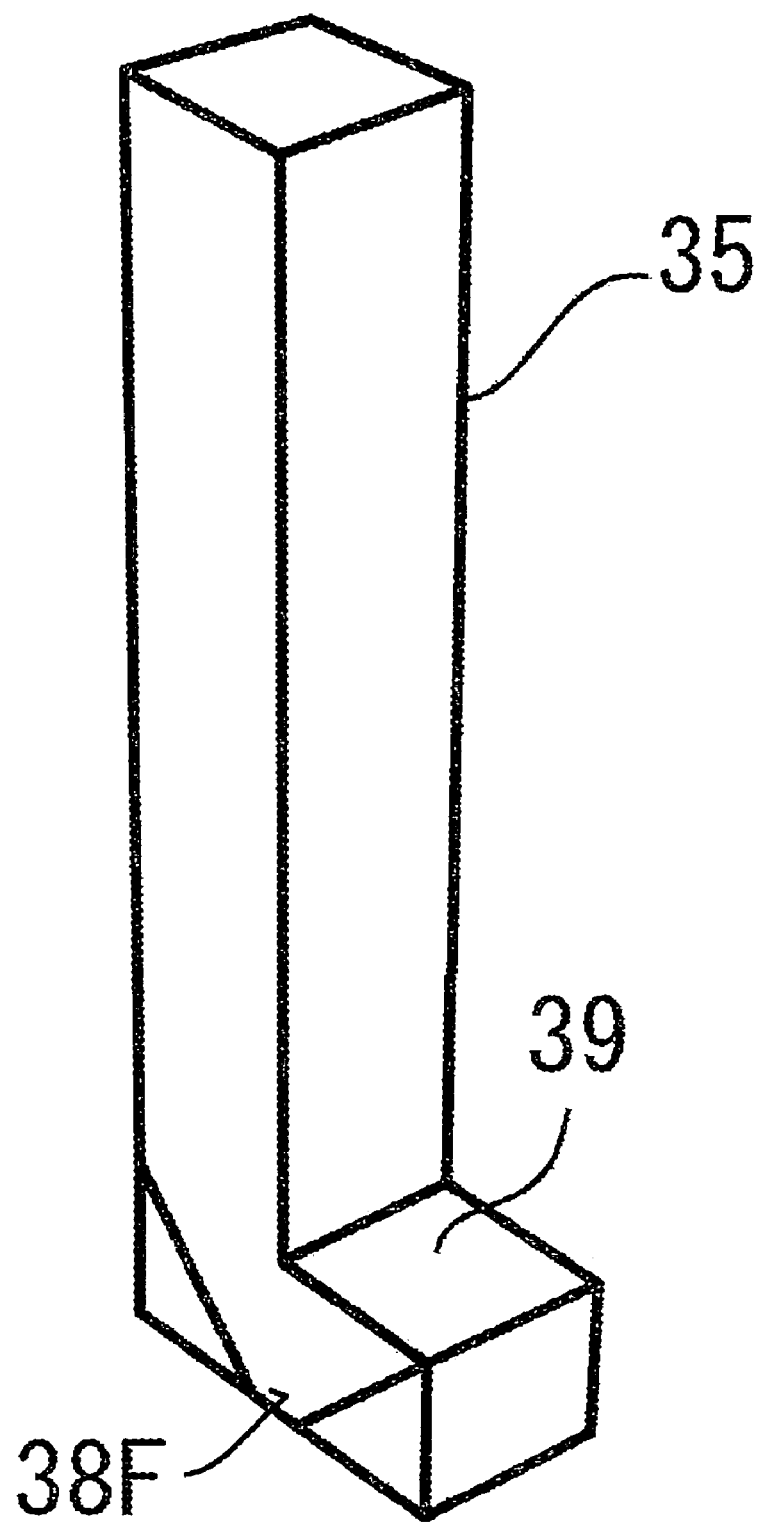
Figures 2, 3, 4:
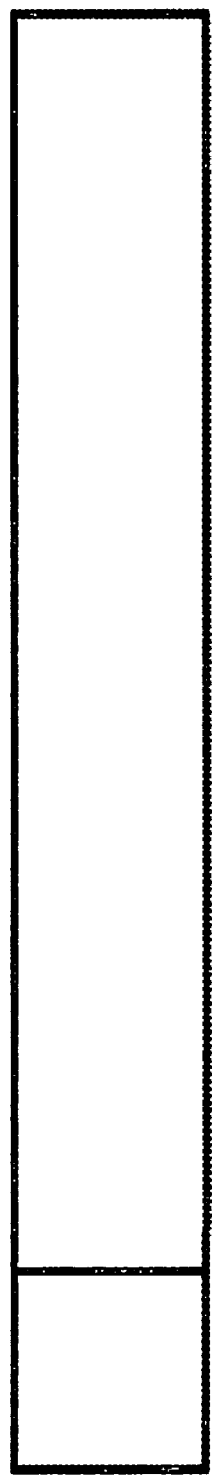

FIG. 2-3 is a perspective view showing the example of arrangement of the observation optical system specific for obtaining a bottom face image, shown in FIG. 2-2. The present invention is a multidirectional simultaneous observation optical system having at least one of one, two or more side face imaging prism systems for obtaining side face images of one, two or more side faces of an object to be inspected and a bottom face imaging prism system for obtaining a bottom face image, as described above. Therefore, the observation optical system specific for obtaining a bottom face image, which is basically constituted by an optical path length correcting prism 35 and an optical path direction changing prism or an optical path direction changing prism function portion 38F, as shown in these figures, is also within the scope of the present invention. In this observation optical system, only a bottom face image is obtained from the prism system, while a planar (top face) image is obtained above an object mount portion 39, that is, two images in total are obtained. In a case where there is no need to obtain side face images while a bottom face image is required, this observation optical system specific for obtaining a bottom face image is a necessary and sufficient arrangement. FIGS. 24 to 2-7 are a front view, a rear view, a bottom view and a plan view, respectively, of the example of arrangement shown in FIG. 2-2.

In the multidirectional simultaneous observation optical system of the present invention, the number of side face imaging prism systems constituting the observation optical system is not limited to a particular number. For example, the number of prism systems may be one of 2, 3, 4, 5, 6 and 7. However, the number of prism systems may be 8 or larger.

FIG. 3 is a perspective view showing an arrangement for obtaining image information on six faces as an example of arrangement of the multidirectional simultaneous observation optical system of the present invention.

Figure 4A:
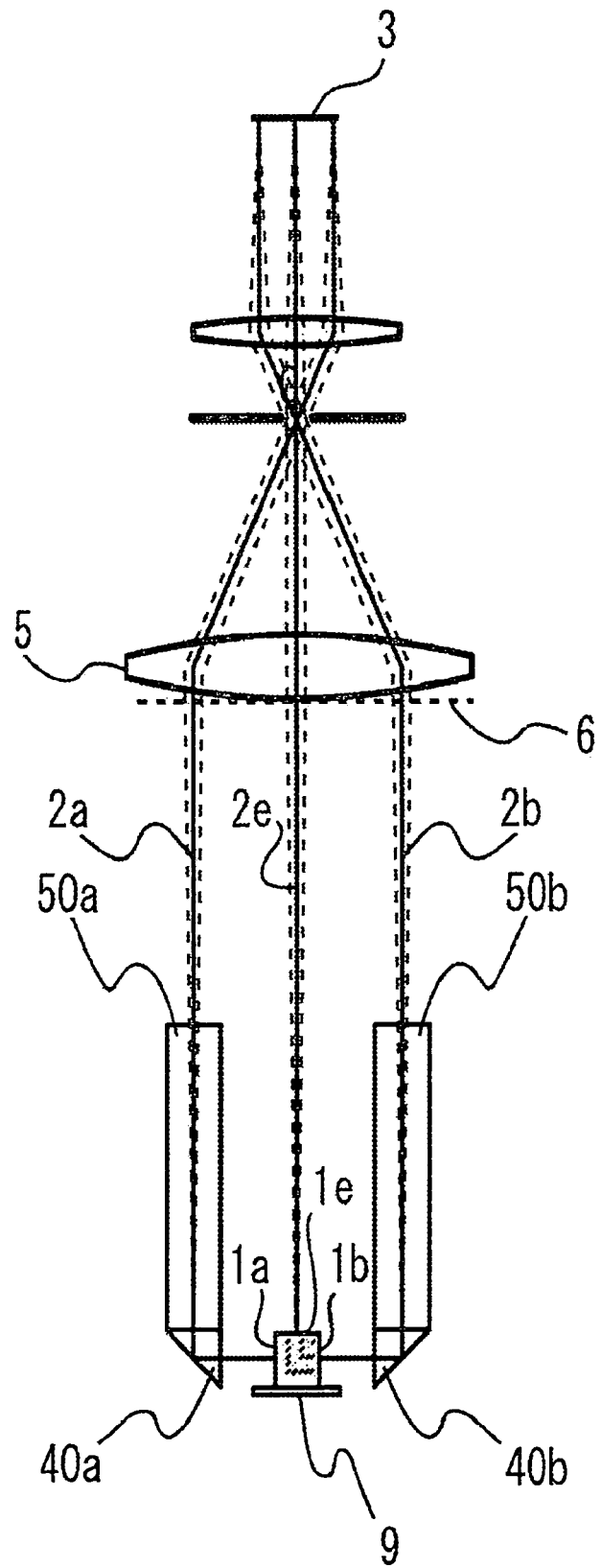
FIG. 4(A) is a longitudinal sectional view taken along cutting line A-A or A'-A' in FIG. 3, which is an explanatory diagram showing a situation in which imaging is achieved.

FIG. 4(A) is a longitudinal sectional view taken along cutting line A-A or A'-A' in FIG. 3, which is an explanatory diagram showing a situation in which imaging is achieved.

Figure 4B:
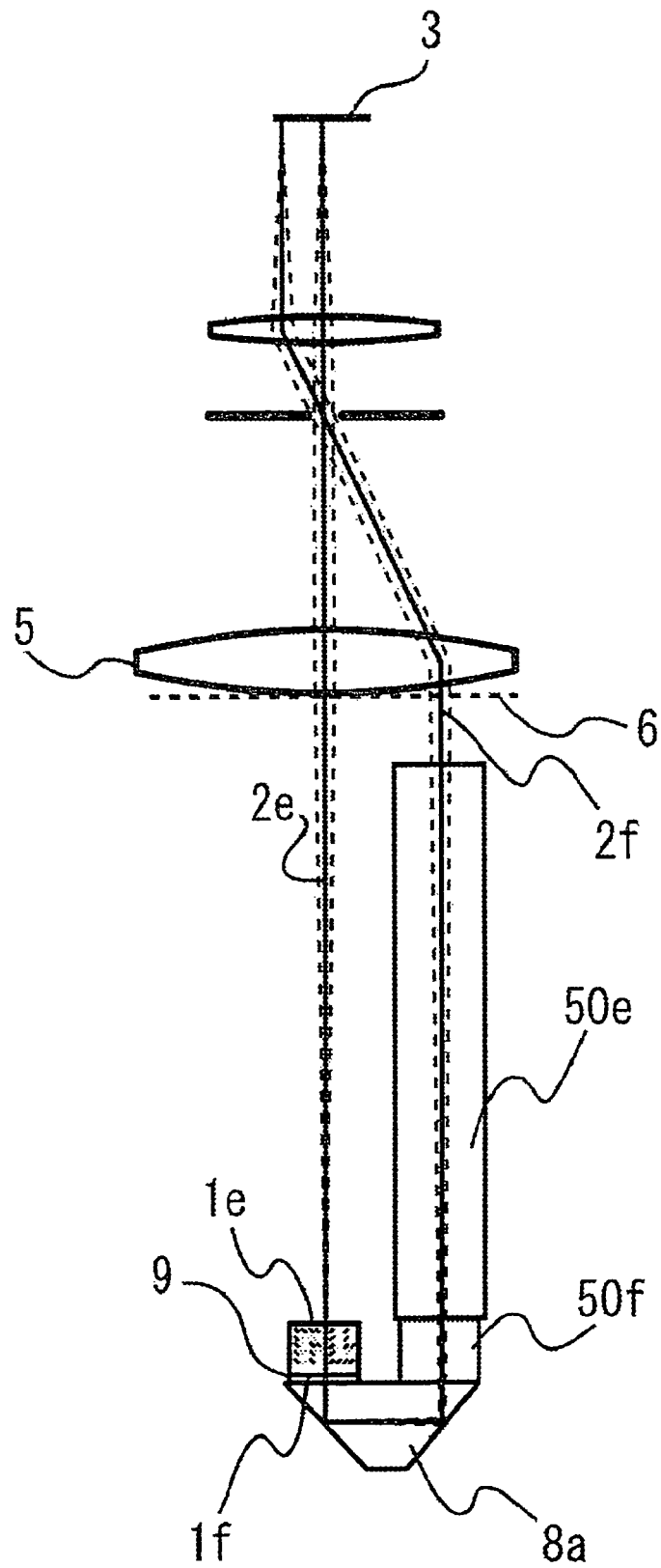
FIG. 4(B) is a longitudinal sectional view taken along cutting line B-B in FIG. 3, which is an explanatory diagram showing a state in which imaging is achieved.
Figure 5:
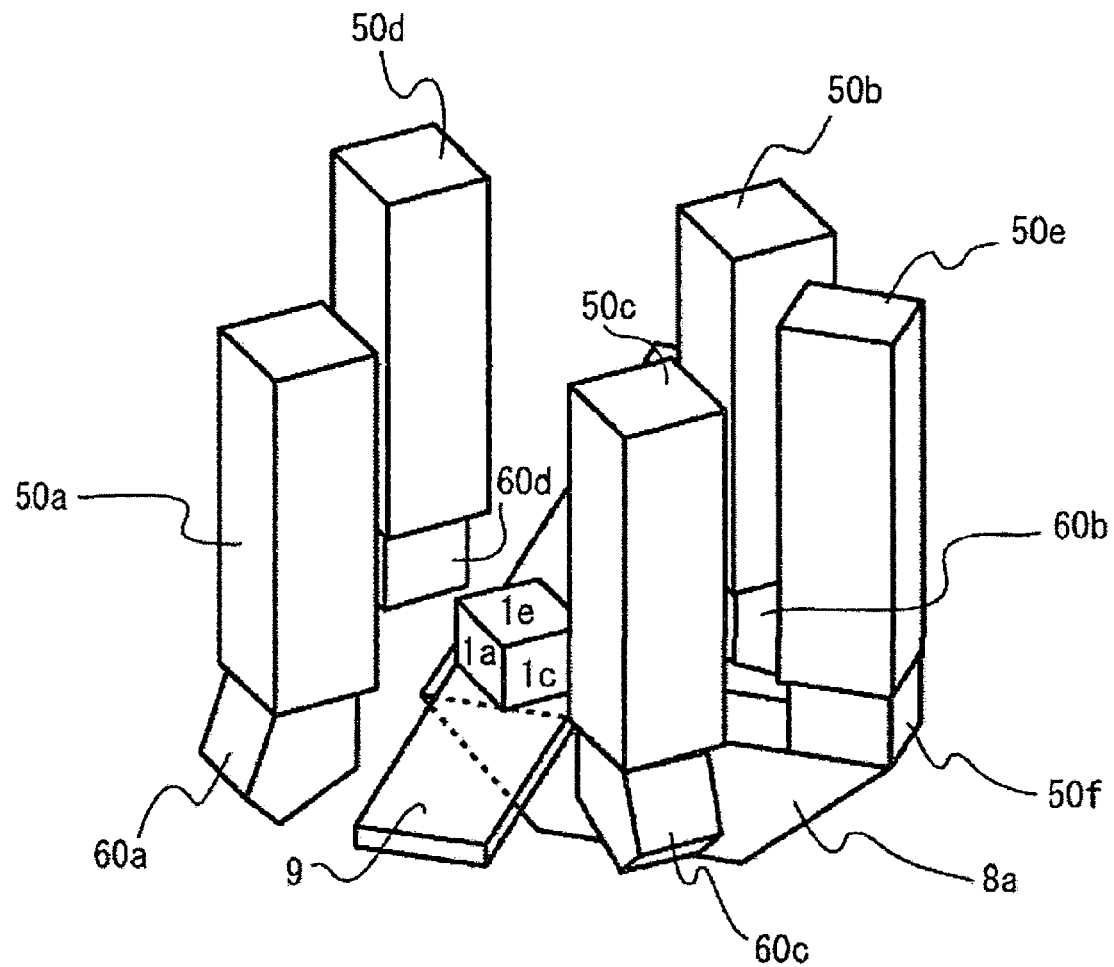

FIG. 4(B) is a longitudinal sectional view taken along cutting line B-B in FIG. 3, which is an explanatory diagram showing a state in which imaging is achieved.

Referring to these figures, as the optical path direction changing prism and so on, the multidirectional simultaneous observation optical system can use 45° mirror prisms 40a, 40b, 40c, and 40d or prisms having the corresponding function (hereinafter also referred to collectively as "45° mirror prism") in the side face imaging prism systems, and a trapezoidal prism 8a or a triangular prism capable of changing the direction two times or a prism having the corresponding function (hereinafter also referred to correctively as "trapezoidal prism") in the bottom face imaging prism system.

The arrangement shown in these figures is only an example of an arrangement for obtaining image information from six faces, suitable for simultaneously observing in many directions objects to be inspected, including a cube, external appearances of which can be grasped in directions from six faces. The present invention is not limited to this number of faces. In these figures, reference symbols 50a, 50b, . . . , 50f denote optical path length correcting prisms. Also, reference numeral 5 denotes a lens; reference numeral 6 a lens end surface; reference numeral 3 an image plane on which the object is imaged.

A further description will be made of obtaining side face and top face images of the object to be inspected in the multidirectional simultaneous observation optical system of the present invention with reference to FIGS. 4(A) and 3.

The velocity of light propagating in glass is higher than the velocity of light propagating in air. That is, the optical path length in glass is reduced when converted into an optical path length in air. Accordingly, the WD 2a from the side face 1a of the object to be inspected to the lens end surface 6 and the WD 2e from the top face 1e of the object to be inspected to the lens end surface 6 differ from each other.

The optical path length correcting prism 50a is placed in the optical path from the side face 1a of the object to be inspected to the lens with the longer distance 2a to equalize the distances 2a and 2e in terms of optical path length in air, thereby enabling the in-focus planes for the side face 1a and the top face 1e in the faces of the object to be inspected to coincide with each other in a common reading device.

The WDs of the side faces 1a and 1b in the faces of the object to be inspected are in different directions but have distance values 2a and 2b equal to each other. Therefore, the optical path length correcting prisms 50a and 50b in accordance with the same specification may be placed for simultaneous observation of the faces of the object to be inspected. The optical path length correcting prisms 50a, 50b, 50c, and 50d are arranged on the basis of the common specification according to the same principle, thus facilitating simultaneous observation of the faces in four directions of the object to be inspected.

Figure 14:
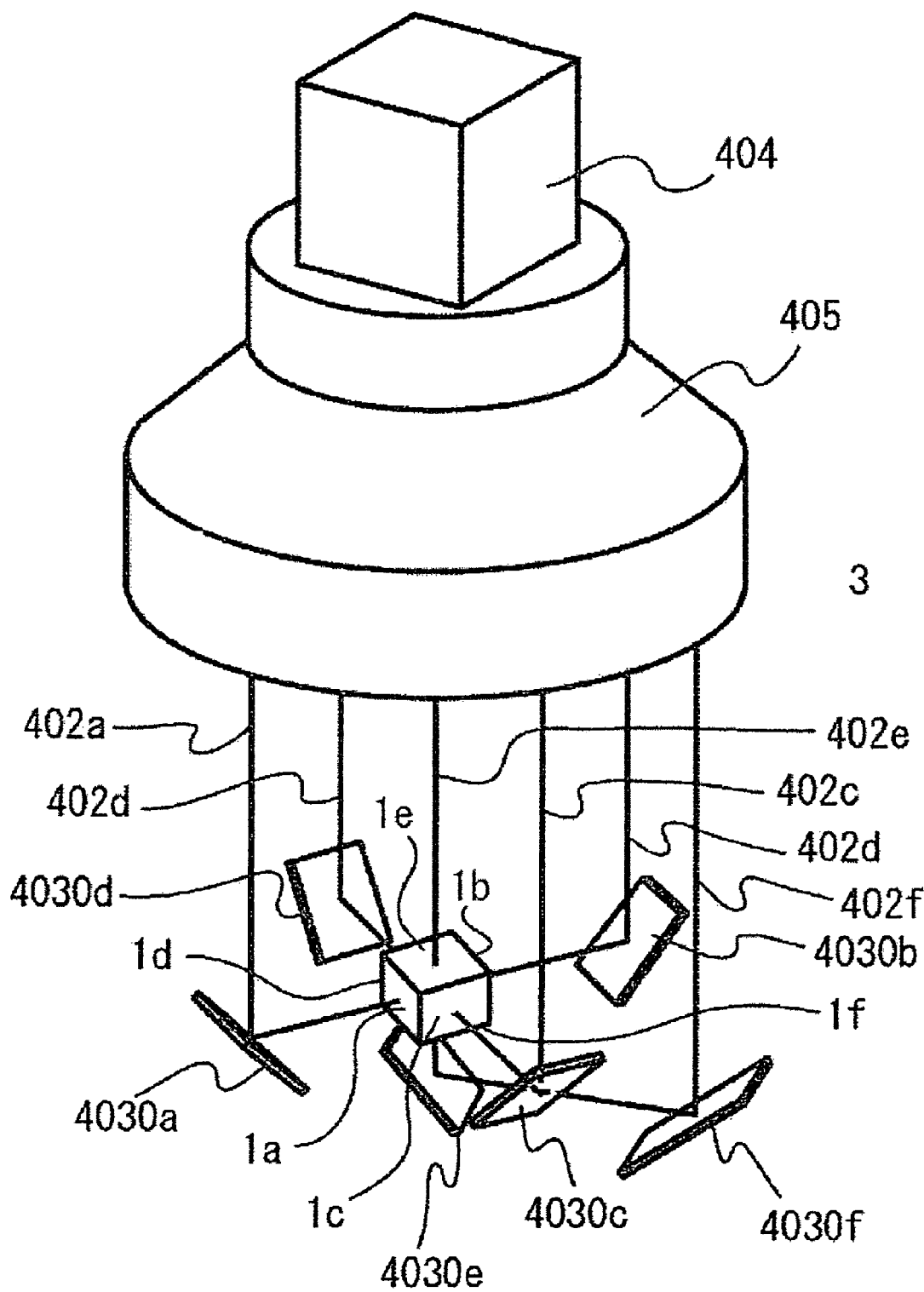
FIG. 14 is an explanatory diagram showing the arrangement of components of a system in which the components are arranged to observe in many directions an object to be inspected while the number of reading devices is reduced to reduce the cost.

The use of the 45° mirror prisms 40a, 40b, 40c, and 40d different from the plane mirrors 4030a to 4030f in the conventional arrangement described above with reference to FIG. 14 ensures that the size of the optical path length correcting prisms 50a, 50b, and so on can be reduced.

In the multidirectional simultaneous observation optical system, an object carrying means 9 may be placed below the object to be inspected in order to hold the object to be inspected and to enable the same to be moved, as described below. The object carrying means 9 may be formed by using a transparent material such as glass to enable a bottom face image of the object to be inspected to be obtained therethrough. If glass is used, the object carrying means will be referred to as "object carrying glass plate" as occasion demands. The object carrying glass plate 9A on which a plurality of objects to be inspected are mounted may be moved in its longitudinal direction by a suitable means to enable the plurality of objects to be inspected to be continuously observed and inspected with efficiency.

A further description will be made of obtaining top face and bottom face (lower face) images of the object to be inspected in the multidirectional simultaneous observation optical system of the present invention with reference to FIGS. 4(B) and 3.

The trapezoidal prism (or triangular prism) 8a having two reflecting surfaces is placed below the object to be inspected and the object carrying glass plate 9 to bend the optical path toward the lens 5 by reflecting the optical path two times.

The optical path length correcting prisms 50f and 50e and the trapezoidal prism (or triangular prism) 8a having two reflecting surfaces are placed so that the distances of the WD 2f from the lower face 1f of the object to be inspected to the lens 5 and the WD 2e from the upper face 1e of the object to be inspected to the lens 5 are equal to each other in terms of optical path length in air, as are those in the above-described case of the side faces of the object to be inspected. The in-focus planes with respect to the object to be inspected are thereby made to coincide with each other to enable the lower face 1f and the upper face 1e of the object to be inspected to be simultaneously observed in the common reading device. That is, the in-focus planes for the lower face 1f and the upper face 1e of the object to be inspected can be made to coincide with each other in the common reading device.

Referring to these figures, the above-described space (9) for carrying the object to be inspected can be secured by adjusting the distance between the optical path length correcting prisms 50a and 50b and the distance between the optical path length correcting prisms 50d and 50c.

In the multidirectional simultaneous observation optical system of the present invention, the upper and lower faces and the side faces in four directions of the object to be inspected, the six faces in total can be simultaneously observed by one reading/imaging device, as described above with reference to FIGS. 3, 4(A), and 4(B). As shown in FIG. 3, the components (prisms) are placed so as to avoid interference therebetween. Therefore, each of the six optical paths is not blocked by any of the other optical paths and no image eclipse occurs.

Figures 2, 3, 4, 5:
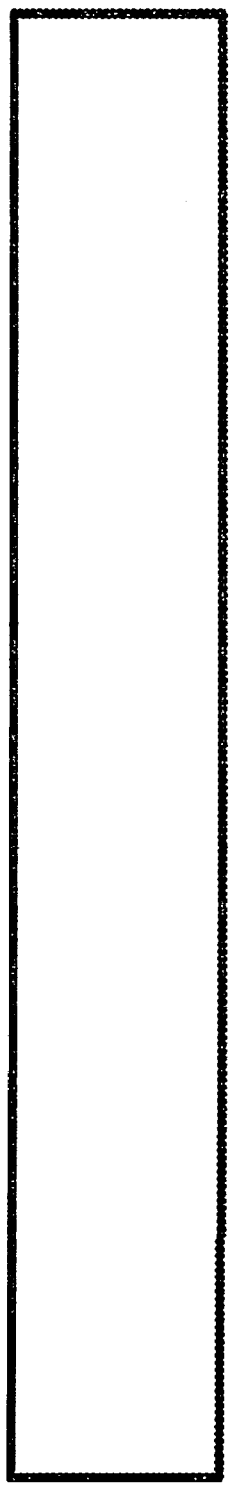

FIG. 5 is a perspective view showing an example of a basic arrangement of a multidirectional simultaneous observation optical system of the present invention for obtaining erect images. Referring to the figure, a penta prism 60a and so on capable of obtaining an erect image or a prism having the corresponding function (hereinafter also referred to collectively as "penta prism") can be used as the optical path direction changing prism and so on of the above-described side face imaging prism system in this multidirectional simultaneous observation optical system.

"Penta prism" refers to one of pentagonal prisms, particularly a pentagonal prism capable of reflecting an image by bending a beam of incident light through 90° by reflecting the incident light two times in the prism while maintaining the image in the erect status without image inversion. The use of such a penta prism ensures that all images can be obtained as erect images.

The example shown in FIG. 5 will be further described. The penta prisms 60a, 60b, 60c, and 60d are used as optical path direction changing prisms in place of the 45° mirror prism 40a and so on described above with reference to FIG. 3.

In the mirror prism 40a and so on shown in FIG. 3, 90° bending reflection is caused when reflection by a mirror reflecting surface is performed one time. Image formation through the mirror prism will described for confirmation with reference to FIG. 14 referred to above. The images with 402a, 402b, 402c, and 402d reflected one time and the image with 402f reflected two times differ in orientation from each other. If the 45° mirror prism 40a and so on shown in FIG. 3 is replaced with the penta prisms 60a and so on as shown in FIG. 5, the images of the side faces of the object to be inspected can be reflected two times, as are the image of the lower face. As a result, images uniformly oriented, i.e., erect images, can be obtained with respect to all the faces of the object to be inspected.

Figure 6A:
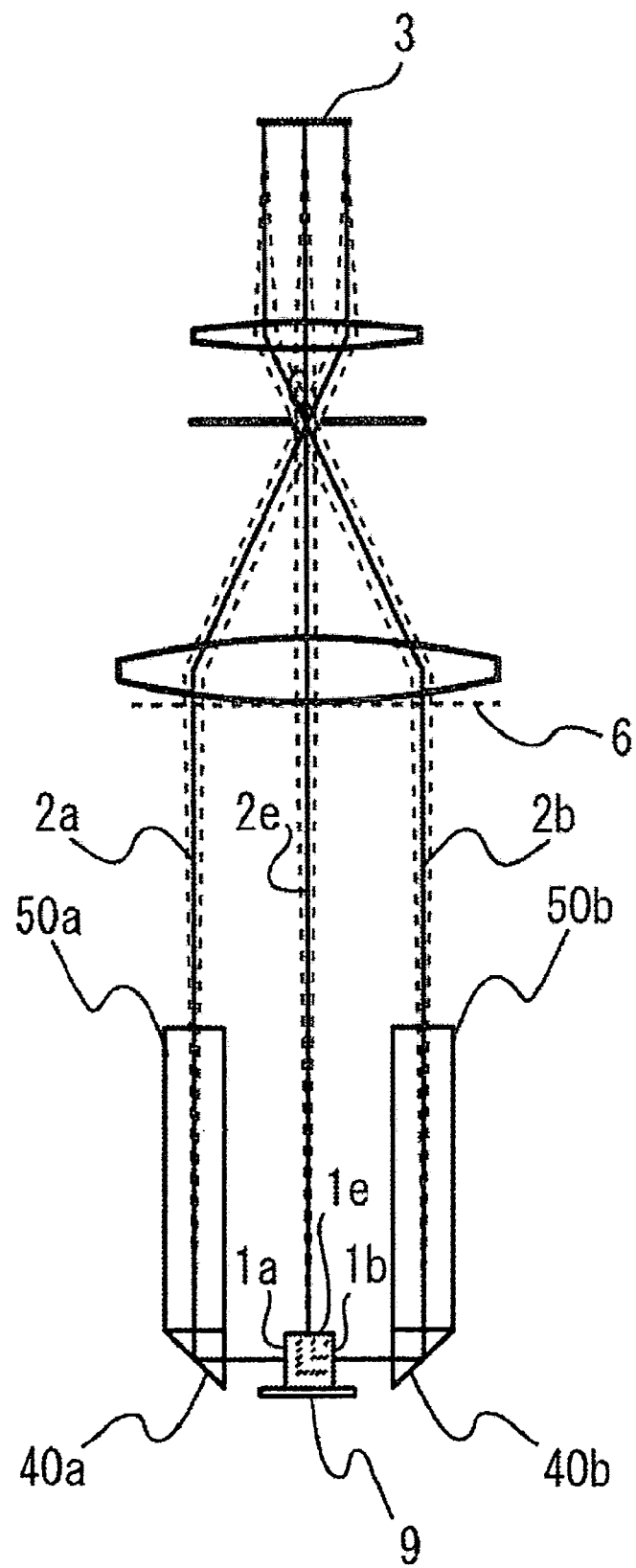
FIG. 6(A) is a longitudinal sectional view of the multidirectional simultaneous observation optical system of the present invention shown in FIG. 3, which is an explanatory diagram showing a situation in which imaging is achieved.
Figures 2, 6:
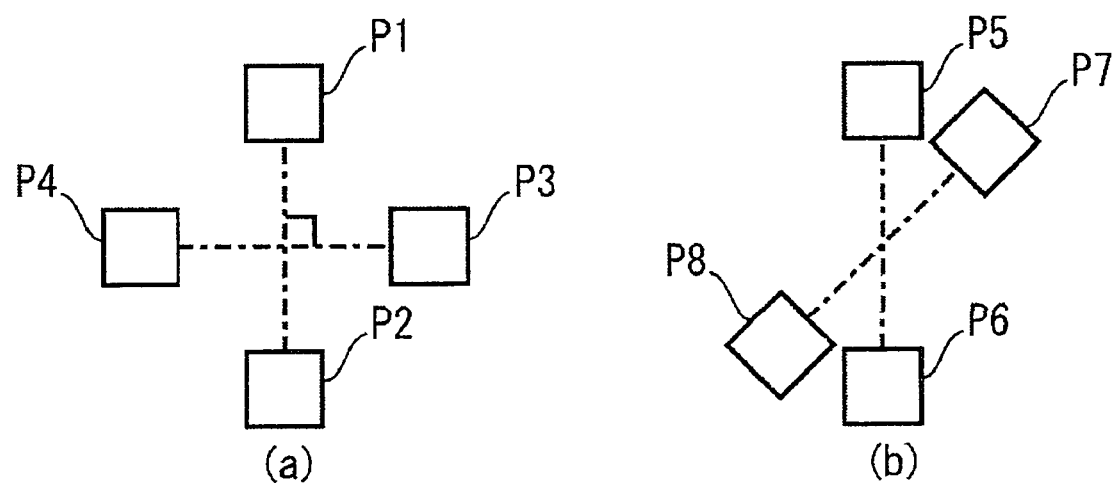
Figure 7:
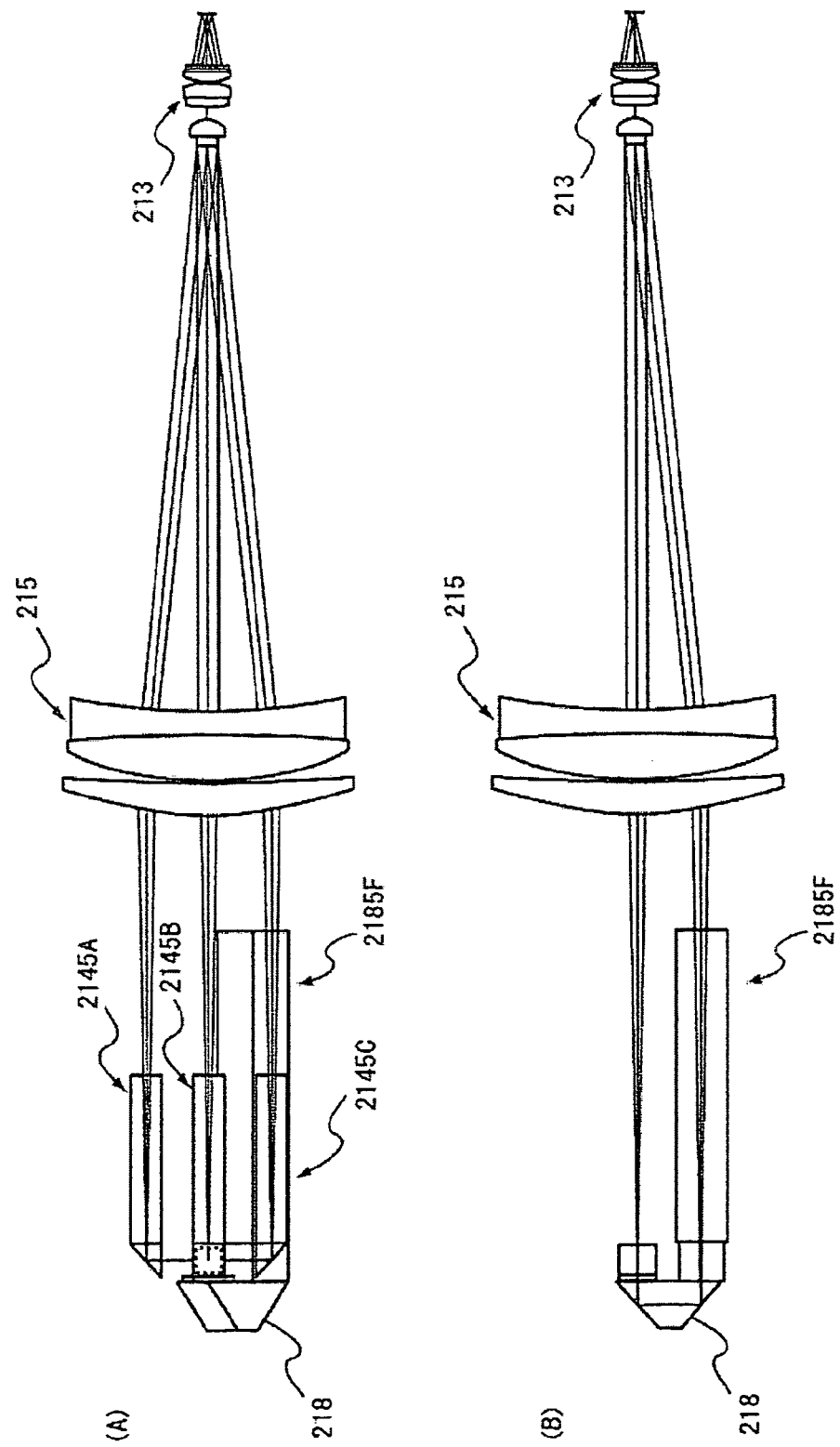

FIG. 6(A) is a longitudinal sectional view of the multidirectional simultaneous observation optical system of the present invention shown in FIG. 3, which is an explanatory diagram showing a situation in which imaging is achieved.

FIG. 6(B) is a longitudinal sectional view of a multidirectional simultaneous observation optical system of the present invention to which another arrangement is added to that in FIG. 6(A), FIG. 6(B) being an explanatory diagram showing a situation in which imaging is achieved. (B-1) in FIG. 6(B) is a longitudinal sectional view of still another multidirectional simultaneous observation optical system of the present invention.

As shown in these figures (FIGS. 6(B) and (B-1) in particular), optical path shifting prisms 70a, 70b, 80a, and so on or an optical path shifting prism function (hereinafter also referred to collectively as "optical path shifting prism") may be provided above the optical path direction changing prism 40a and so on in the prism systems in the multidirectional simultaneous observation optical system. "Shifting" refers to a movement along a direction in a section transversal to the direction of travel of light from the prisms 70a, 70b, and so on, or 80a, 80b, and so on.

Referring to FIGS. 6(B) and (B-1), the optical path shifting prism 70a and so on can be arranged so that the optical path section for optical output from the faces of the object to be inspected is reduced in order to reduce the area of light incident on a lens or the like and to thereby improve the resolution. That is, the optical path shifting prism 70a and so on are arranged so that light traveling upward in the prisms 50a and so on is converged closer to the optical axis center.

A further description will be made with reference to these figures. The optical path shifting prism 70a, 70b, and so on or the optical path shifting mirrors 80a, 80b, and so on are placed above the optical path direction changing prisms 40a and so on and above or below the side-face optical path length correcting prisms 50a to 50d to enable the side face image optical axes to be shifted parallel. If the elements are placed so that the lens incident light area is reduced as described above, an effect of reducing the size of the entire image obtained from the object to be inspected can be thereby achieved. The size per pixel of the object image taken by an image pickup device can be reduced to improve the resolution. As a result, observation with improved resolution can be performed while the same image pickup device is used.

As shown in FIGS. 3 and 5 and other figures, the object carrying means 9 on which two or more objects to be inspected are mounted and which is capable of carrying and moving the objects via the above-described object mount space portion can be provided in the multidirectional simultaneous observation optical system of the present invention, and the above-described prism systems 50a, 50e, and so on can be arranged by being placed so that the carriage path for the object carrying means 9 is secured.

Four side face imaging prism systems are provided in the multidirectional simultaneous observation optical system of the present invention, as are those illustrated in the figures, and the multidirectional simultaneous observation optical system can be arranged so as to be capable of obtaining image information in the form of light on the regular six faces of an object to be inspected including the top face from which an optical output can be obtained without the above-described prism systems. Grasping appearances of an object to be inspected with respect to the six faces, as ordinarily used for identification of a design in an industrial property right procedure, usually satisfies conditions for appearance identification in an inspection or the like. Therefore, the above-described arrangement is of certain usage value.

Figures 2, 3, 4, 5, 6:
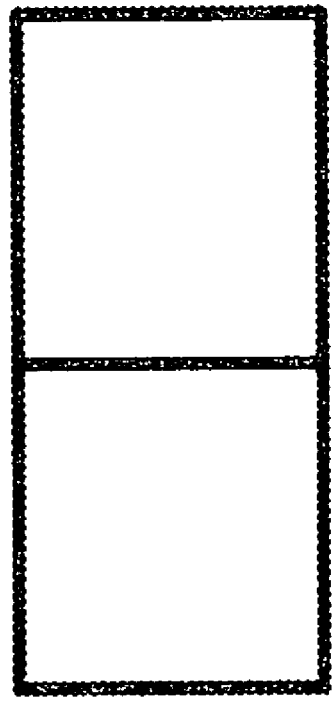
Figures 2, 3, 4, 5, 6, 7:
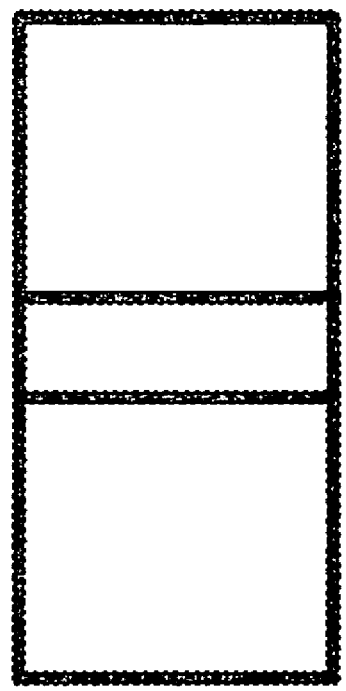
Figure 3:
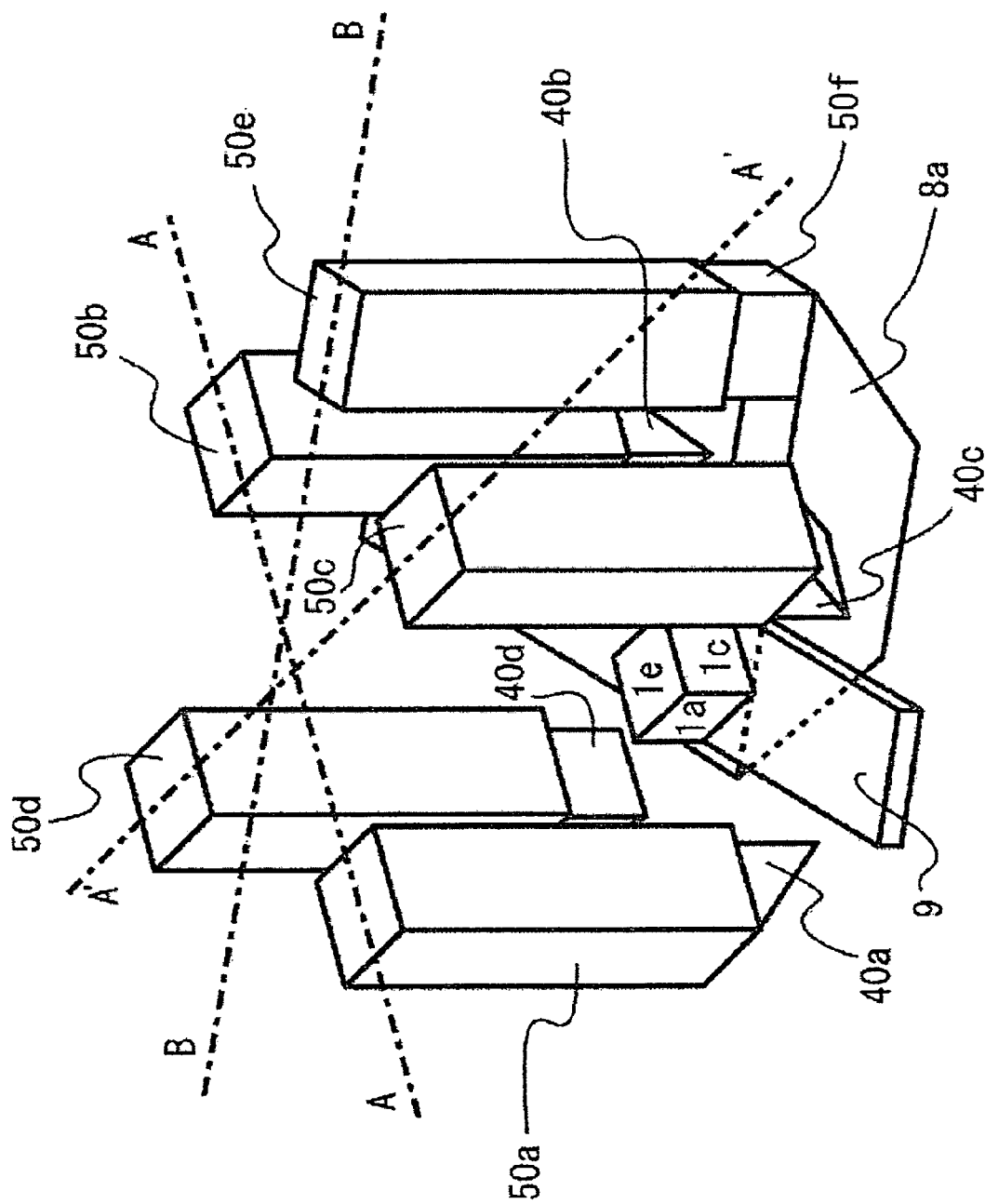

FIG. 6-2 is a plan view showing an example of placement in the multidirectional simultaneous observation optical system of the present invention. An arrangement is conceivable in which, as shown in the figure, two pairs of side face imaging prism systems opposed to each other with the above-described object mount space portion interposed therebetween are placed as the four side face imaging prism systems orthogonally to each other (P1, P2, P3, and P4) (FIG. 6-2(a)). Another arrangement is conceivable in which the two pairs of prism systems are placed at any angle (P5, P6, P7, and P8) (FIG. 6-2(b)).

According to the present invention, an arrangement may be adopted in which three or more pairs of systems comprising the above-described opposed pair of systems are placed. In a case where three pairs of systems are placed, the faces of a polyhedral body having seven or more faces including five side faces can be simultaneously observed.

As described above with reference to the figures, the multidirectional simultaneous observation optical system of the present invention may be defined as a system including a lens provided in the optical output direction from the side face imaging prism systems and the bottom face imaging prism system, or a system without such a lens.

A telecentric lens capable of forming a telecentric system on the side of the object to be inspected may be used as the above-described lens to form a system capable of accurately performing image measurement such as size measurement. The use of the telecentric lens makes it possible to reduce the size of each prism constituting the optical system as well as to reduce the size of the entire optical system constituted by the prisms.

As the above-described lens, a lens having a depth of field sufficient for simultaneously adjusting the in-focus planes for the faces even with respect to a complicated object to be inspected having a spherical or hyper-polyhedral shape or the like may be specially used.

Various shapes of objects to be inspected may exist. The description has been made mainly of the cubic shape shown in FIG. 1 as a model for the object to be inspected. In a case where the object to be inspected has the shape of a rectangular block having sides of different lengths, or a shape similar to the shape of such a rectangular block, however, the size of the optical path length correcting prism 50a and so on may be changed to a suitable value to enable all the faces of the object to be inspected to be simultaneously focused (see FIGS. 3, 4(A), and 4(B) for example).

In a case where the object to be inspected is a specially shaped polyhedral body having parallel upper and lower faces and five or more side faces for example, the system may be modified by increasing the number of sets of side-face optical path length correcting prism 50a and so on and 45° mirror prisms 40a and so on in correspondence with the number of side faces.

In a case where the object to be inspected is a spherical body or a hyper-polyhedral body having an extremely large number of faces, the depth of field of the lens of the reading device may be increased as mentioned above to enable focusing of the in-focus planes with respect to the spherical or hyper-polyhedral body and to achieve the effect of the present invention.

Even in a case where the object to be inspected has one, two or more of such kinds of complicatedness of shapes, the system may be modified by selecting a suitable combination of a) the method of changing the size of the optical path length correcting prism 50a and so on to a suitable value,
b) the method of increasing the number of sets of optical path length correcting prism 50a and so on and 45° mirror prisms 40a and so on in correspondence with the number of side faces, and
c) the method of increasing the depth of field of the lens, or selecting one of these methods.

FIG. 7 is an explanatory diagram showing a principle-arrangement of an image reading device of the present invention, (A) mainly showing side face imaging prism systems, (B) mainly showing side face imaging prism systems.

Referring to the figure, the multidirectional simultaneous observation optical system is constituted mainly by side face imaging prism systems 2145A, 2145B, and so on, and a bottom face imaging prism system 2185F. The principle-arrangement of the image reading device includes one of the above-described multidirectional simultaneous observation optical systems, an electronic image pickup device 213 such as a CCD, a CMOS or a line CCD for making photoelectric conversion processing of light obtained through the lens 215. If a line CCD is used, faces of a lengthwise object to be inspected, e.g., an object in linear form can be simultaneously observed continuously while moving the object.

The image reading device in this arrangement can be used for image analysis including image measurement in combination with a suitable piece of software such as a piece of image analysis software.

The principle-arrangement shown in (A) and (B) of FIG. 7 is used to obtain image information in the form of light on the faces of an object to be inspected through the multidirectional simultaneous observation optical system constituted by 2145A, 2185F, and so on, to obtain electrically processible image information by performing photoelectric conversion processing with the electronic image pickup device 213, e.g., a CCD, a CMOS or a line CCD on the light obtained through the lens 215, and to perform image analysis including image measurement on the image information.

Figure 8:
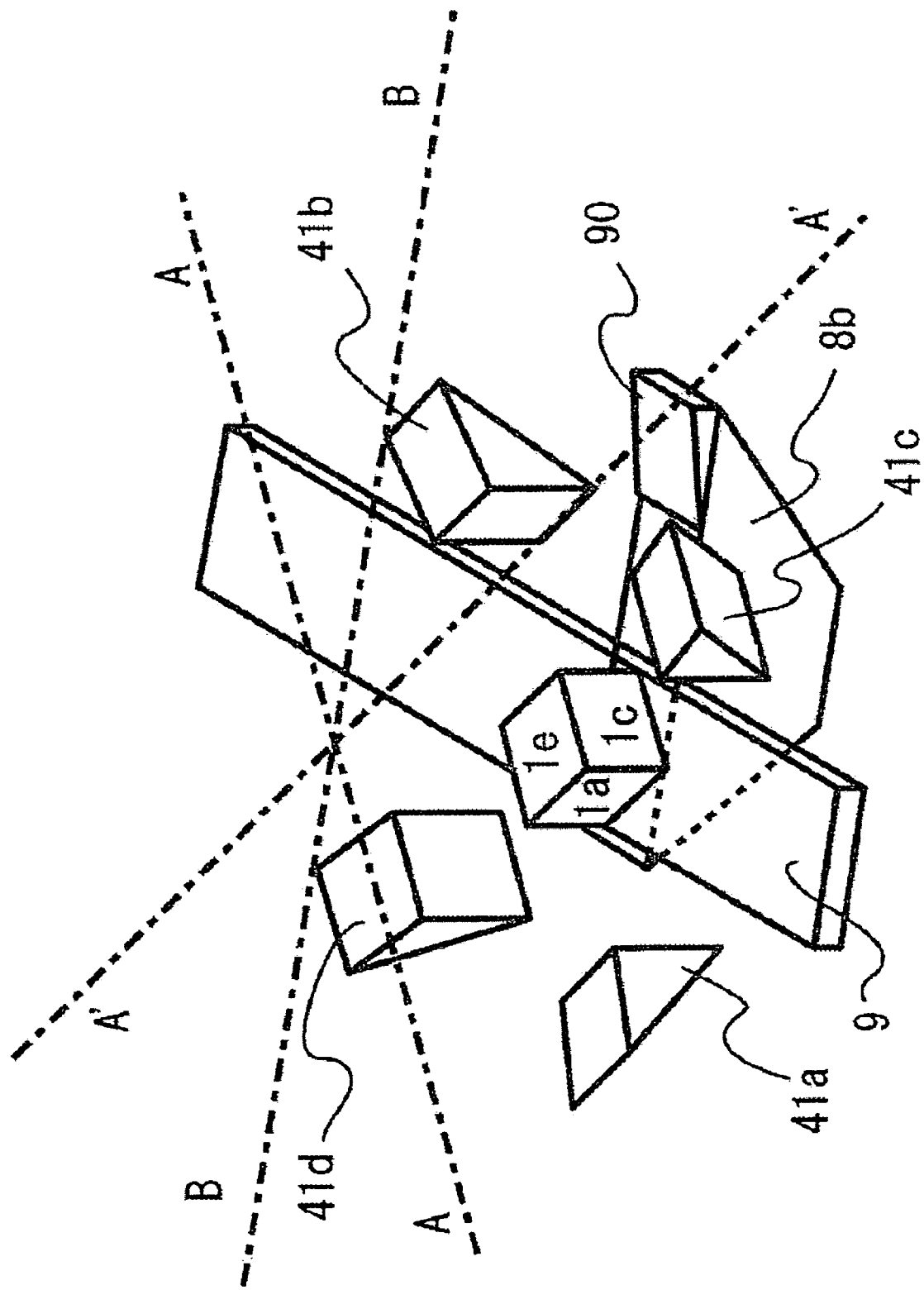
FIG. 8 is a perspective view showing an arrangement usable for observation with the eye as an example of the arrangement of the multidirectional simultaneous observation optical system of the present invention.

FIG. 8 is a perspective view showing an arrangement usable for observation with the eye as an example of the arrangement of the multidirectional simultaneous observation optical system of the present invention.

Figure 9A:
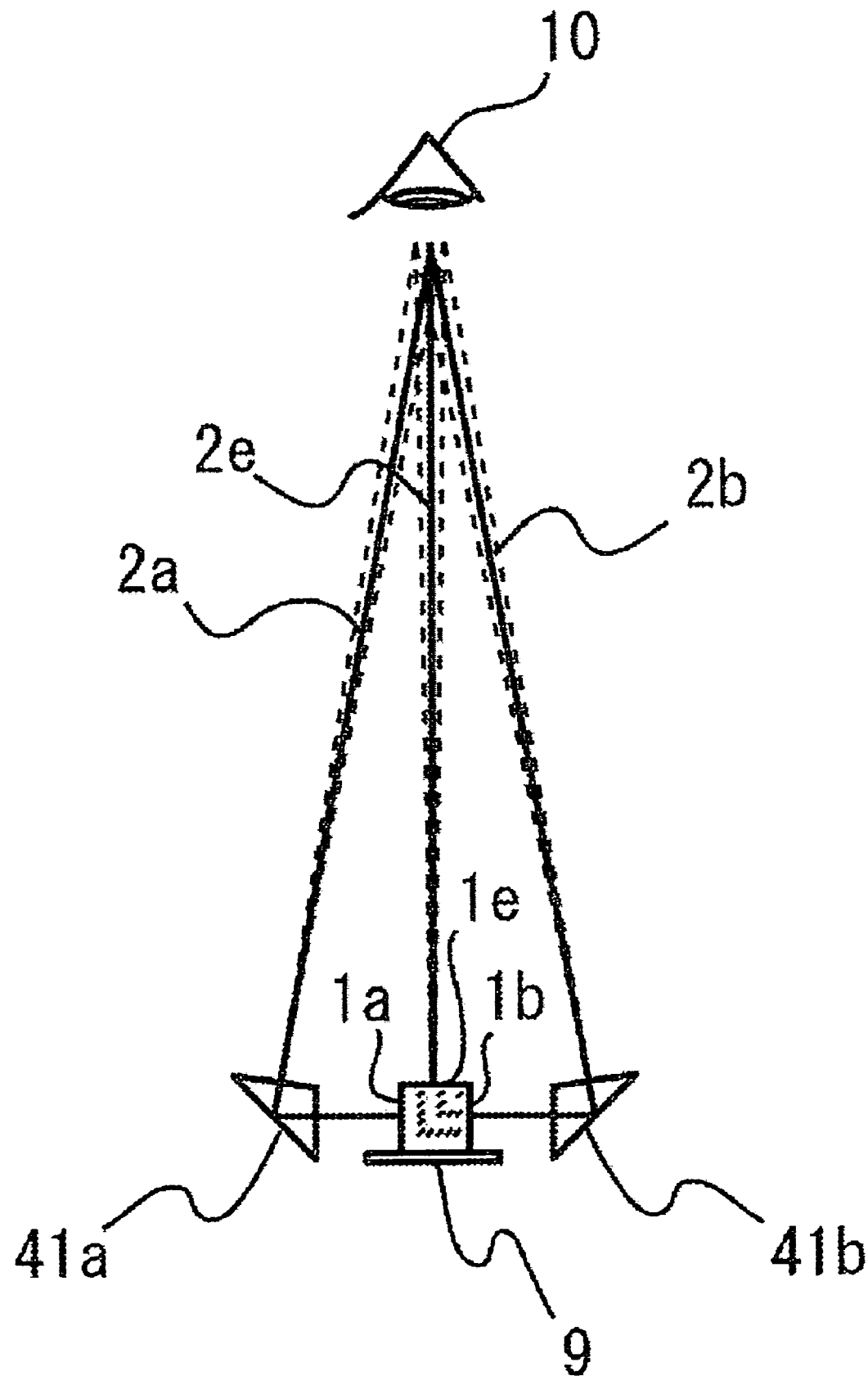
FIG. 9(A) is a longitudinal sectional view taken along cutting line A-A or A'-A' in FIG. 8, which is an explanatory diagram showing a situation where imaging with the human eye can be achieved.

FIG. 9(A) is a longitudinal sectional view taken along cutting line A-A or A'-A' in FIG. 8, which is an explanatory diagram showing a situation where imaging with the human eye can be achieved.

Figure 9B:
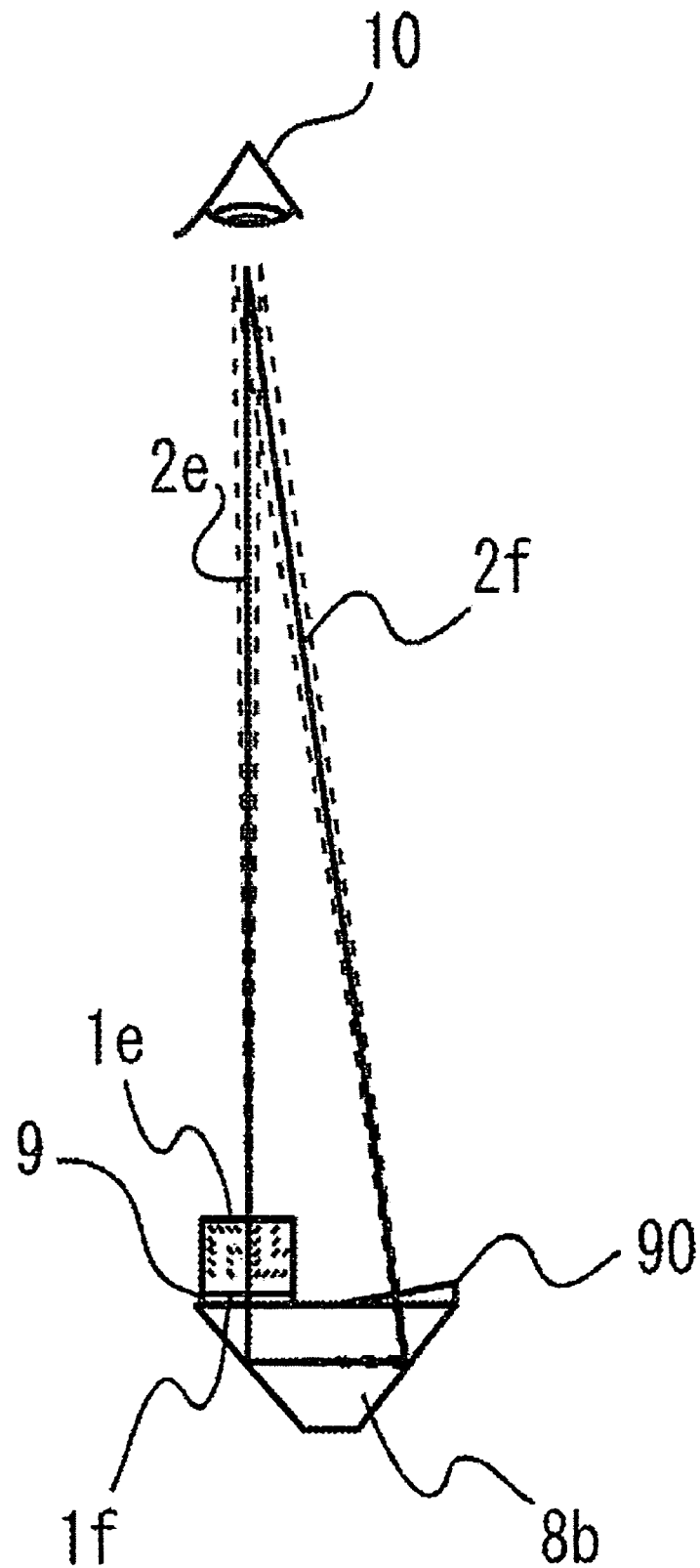
FIG. 9(B) is a longitudinal sectional view taken along cutting line B-B in FIG. 8, which is an explanatory diagram showing a situation where imaging with the human eye can be achieved.

FIG. 9(B) is a longitudinal sectional view taken along cutting line B-B in FIG. 8, which is an explanatory diagram showing a situation where imaging with the human eye can be achieved.

Referring to these figures, this multidirectional simultaneous observation optical system is based on a specific arrangement in which an open space is formed above each of the optical path direction changing prism 41a and so on in the side face imaging prism systems and the bottom face imaging prism system. That is, the above-described optical path length correcting prisms are not provided.

Even the arrangement positively avoiding use of the optical path length correcting prism ensures that multidirectional simultaneous observation of an object to be inspected can be performed adequately and easily as visual observation with the human eye 10. This arrangement is advantageous in terms of cost because of the simplified form and can be provided as a low-priced observation optical system.

Referring to the figures, as the optical path direction changing prism, the multidirectional simultaneous observation optical system can use a triangular mirror prism 41a and so on in the side face imaging prism systems, and a trapezoidal prism 8b, a triangular prism or the like capable of changing the direction two times in the bottom face imaging prism system.

A further description will be made of the illustrated concrete example. The optical path length correcting prism 50a and so on shown in FIG. 3 and so on are removed; the above-described reading device is replaced with the human eye 10; the 45° mirror prism 40a and so on are replaced with triangular mirror prisms 41a, 41b, 41c, and 41d; and an antireflection prism 90 is placed at a position corresponding to the optical path length correcting prism 50f, thus arranging the multidirectional simultaneous observation optical system.

In this way, the size of the optical system of the present invention can be reduced and the arrangement can be simplified. The in-focus planes can be simultaneously adjusted with respect to all the six faces of the object to be inspected, and images of all the six faces of the object to be inspected can be simultaneously provided without any eclipse by placing the prisms constituting the multidirectional simultaneous observation optical system so that each of the optical paths is not obstructed by any of the other optical paths.

This arrangement eliminates the need for the optical path length correcting prism 50a and so on and the reading device and can therefore function adequately as a simplified-type observation optical system in use for visual inspection for example.

Figure 10:
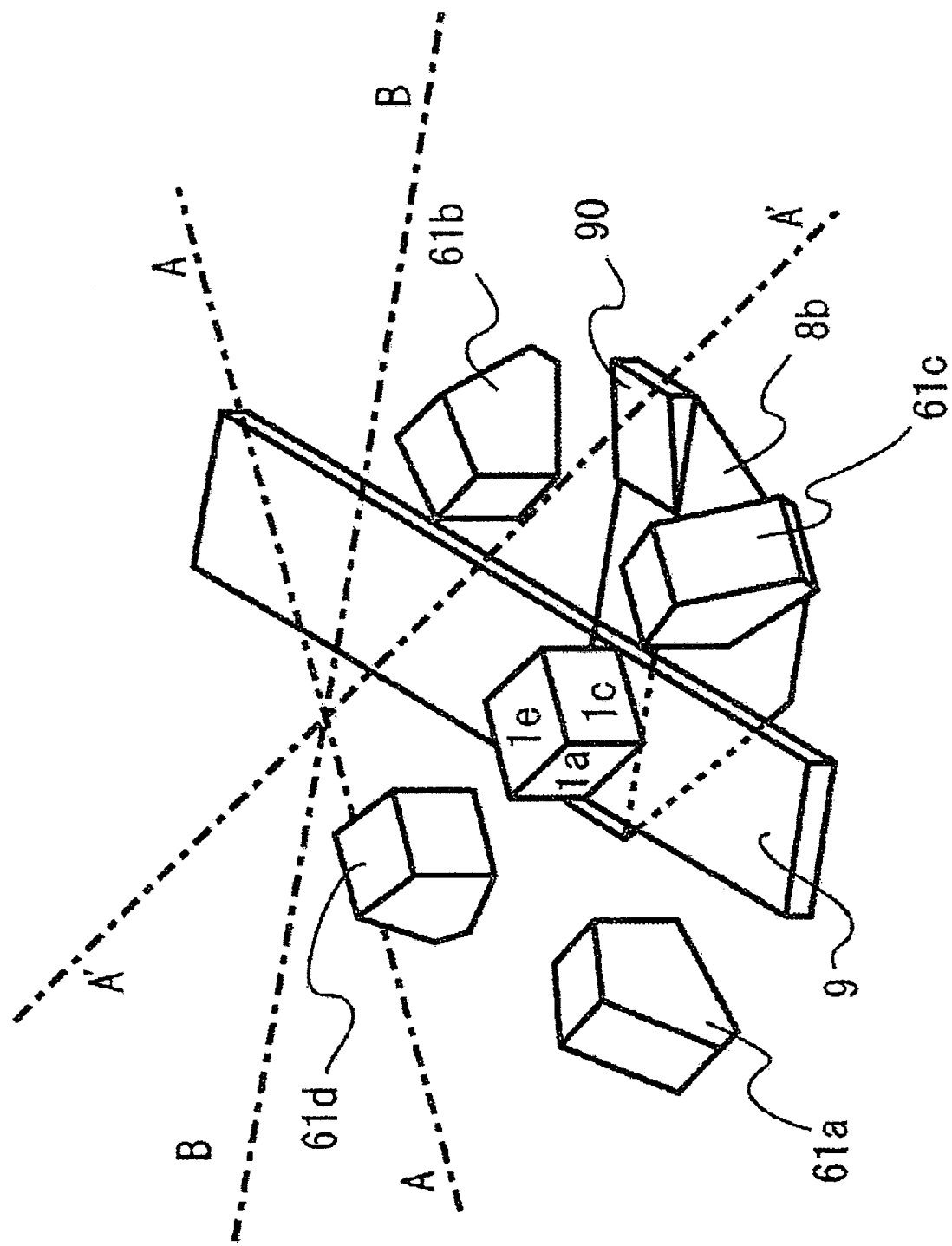
FIG. 10 is a perspective view showing an arrangement using a pentagonal prism as an example of arrangement of a simplified-type multidirectional simultaneous observation optical system of the present invention.

FIG. 10 is a perspective view showing an arrangement using a pentagonal prism as an example of arrangement of a simplified-type multidirectional simultaneous observation optical system of the present invention.

Figure 11A:
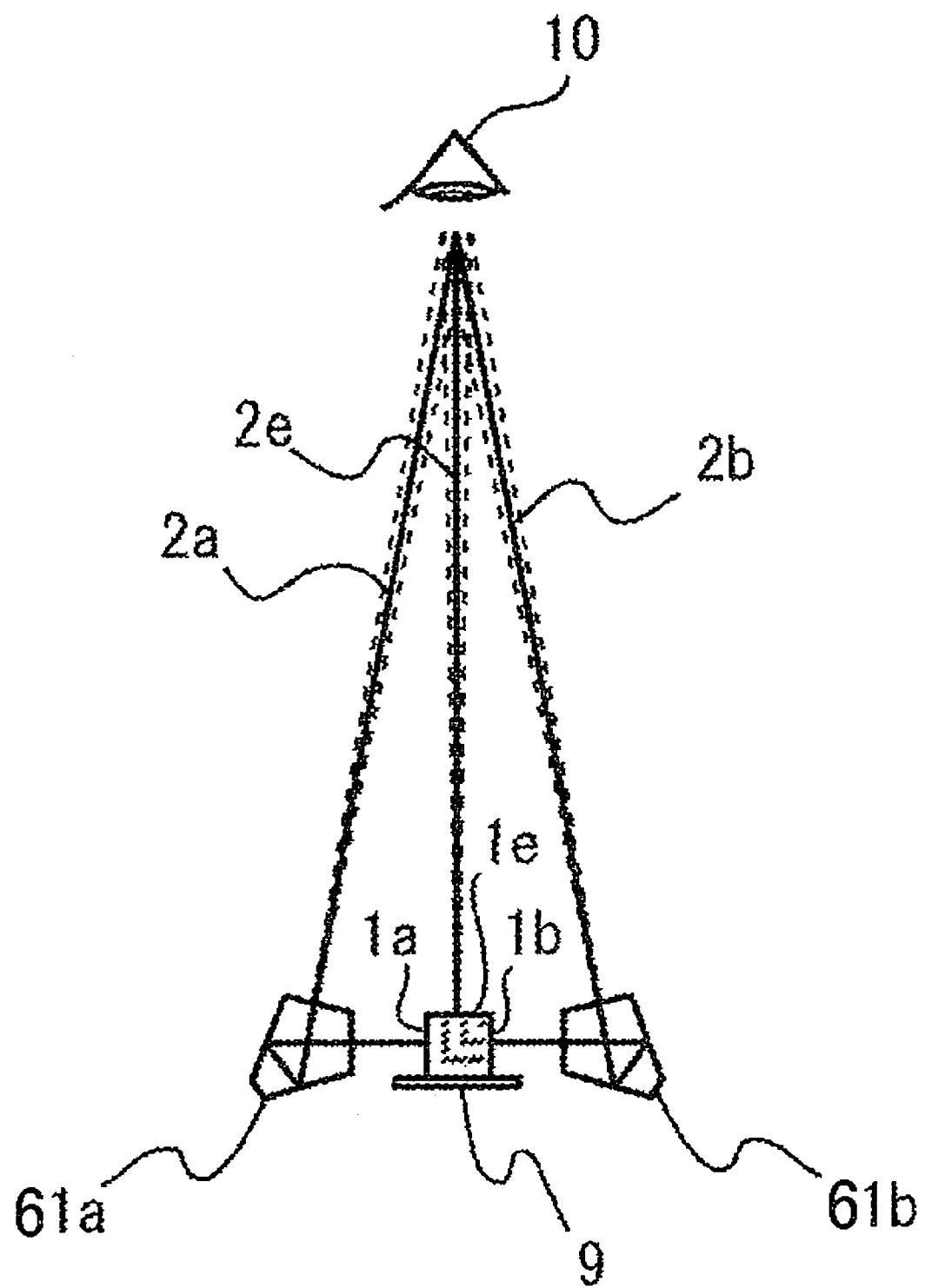
FIG. 11(A) is a longitudinal sectional view taken along cutting line A-A or A'-A' in FIG. 10, which is an explanatory diagram showing a situation where imaging with the human eye can be achieved.

FIG. 11(A) is a longitudinal sectional view taken along cutting line A-A or A'-A' in FIG. 10, which is an explanatory diagram showing a situation where imaging with the human eye can be achieved.

Figure 11B:
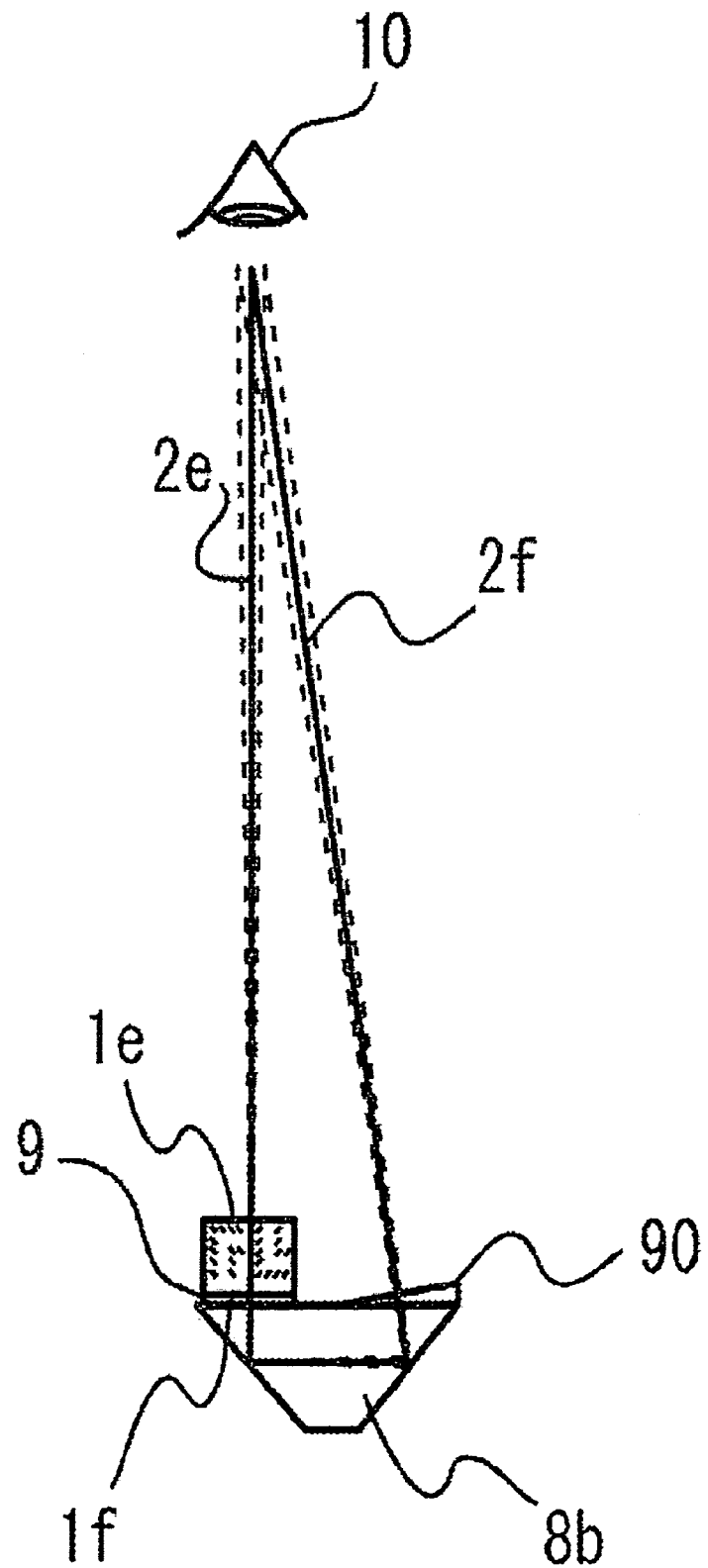
FIG. 11(B) is a longitudinal sectional view taken along cutting line B-B in FIG. 10, which is an explanatory diagram showing a situation where imaging with the human eye can be achieved.
Figure 12:
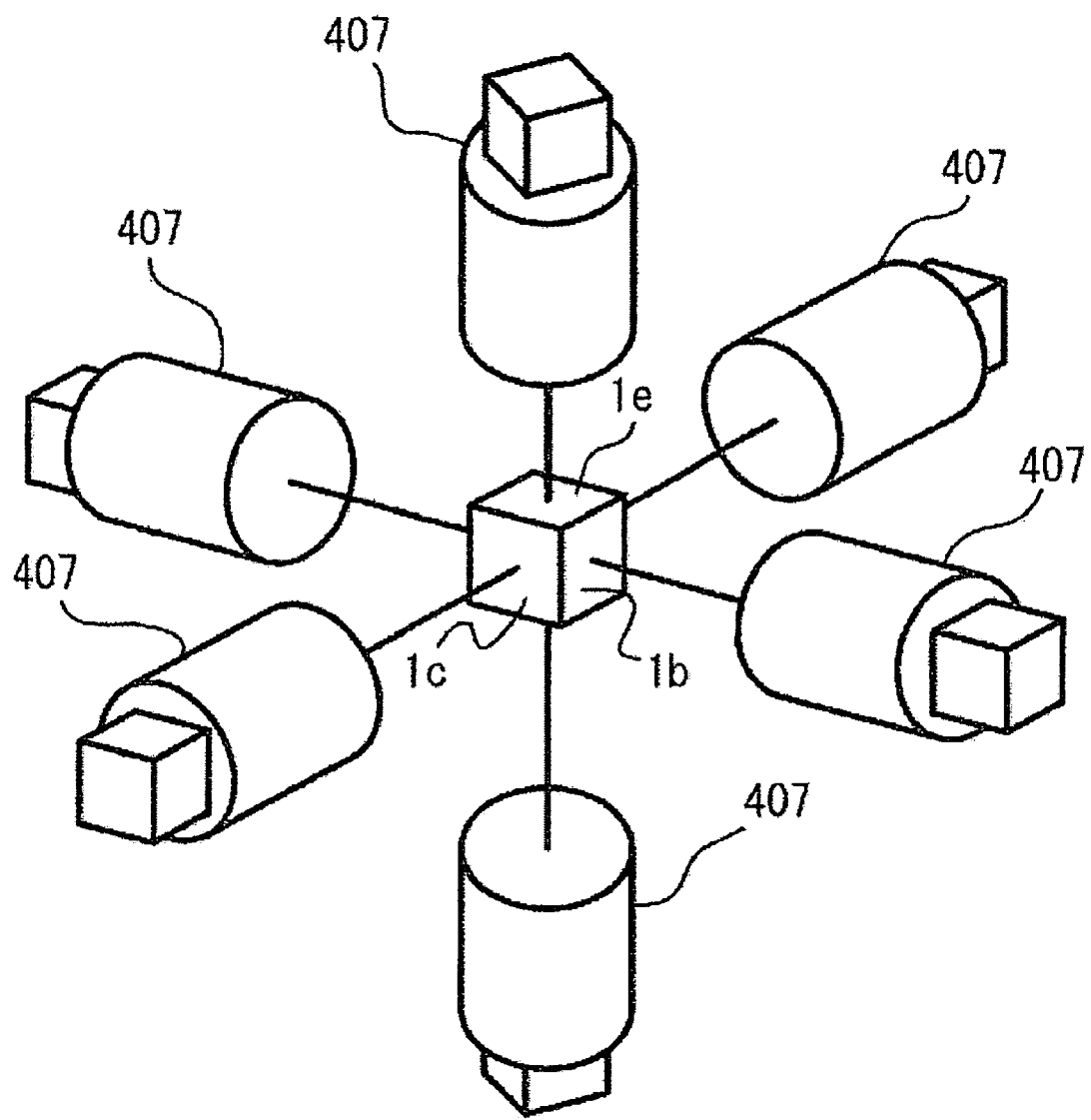
FIG. 12 is an explanatory diagram showing an example of a conventional method of observing in many directions an object to be inspected.
Figure 13:
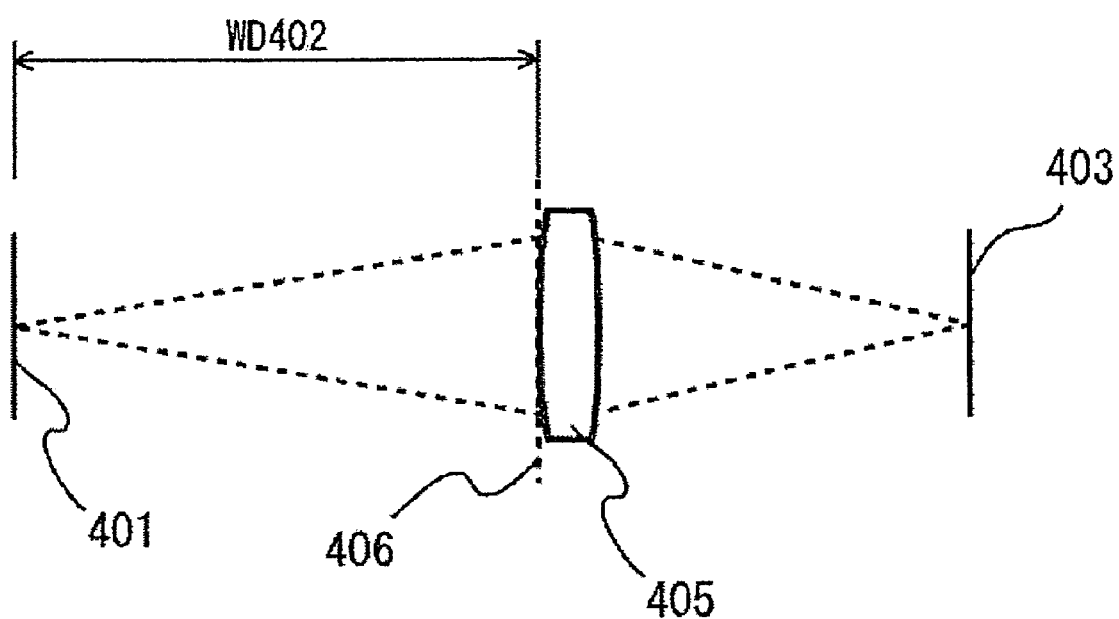
FIG. 13 is an explanatory diagram showing the relationship between a face of an ordinary object to be inspected, a lens and an image plane.

FIG. 11(B) is a longitudinal sectional view taken along cutting line B-B in FIG. 10, which is an explanatory diagram showing a situation where imaging with the human eye can be achieved.

Referring to these figures, a pentagonal prism 61a and so on capable of obtaining an erect image or a prism having the corresponding function may be used as the optical path direction changing prism in the above-described side face imaging prism systems.

The functions and effects of this arrangement are basically the same as those achieved by using the penta prisms described above with reference to FIG. 5. That is, while reflection is caused one time by the mirror reflecting surface in the mirror prism 41a and so on shown in FIG. 8, each of the pentagonal prisms 61a, 61b, 61c, and 61d reflects two times in the arrangement using the pentagonal prisms as shown in FIG. 10 and so on, as does the trapezoidal prism 8b. Thus, images of the faces of the object to be inspected can be uniformly oriented.

As shown in FIGS. 8, 10, and so on, this simplified-type multidirectional simultaneous observation optical system may also be provided with the means 9 for carrying an object to be inspected, on which two or more objects to be inspected are mounted, and which can carry and move the objects to be inspected via the object mount space portion.

As illustrated in the figures, the simplified-type multidirectional simultaneous observation optical system may be arranged by providing four side face imaging prism systems as the above-described side face imaging prism systems so that image information on the regular six faces of the object to be inspected including the top face from which an optical output can be obtained without the above-described prism system can be obtained in the form of light. An arrangement is conceivable in which, as described above with reference to FIG. 6-2, two pairs of side face imaging prism systems opposed to each other with the above-described object mount space portion interposed therebetween are placed as the four side face imaging prism systems orthogonally to each other (P1, P2, P3, and P4) (FIG. 6-2(a)). Another arrangement is conceivable in which the two pairs of prism systems are placed at any angle (P5, P6, P7, and P8) (FIG. 6-2(b)).

The two or more multidirectional simultaneous observation optical systems described above may be used to form a multidirectional simultaneous observation combined optical system enabling multidirectional simultaneous observation of, for example, an object to be inspected having a considerably large size.

INDUSTRIAL APPLICABILITY

The multidirectional simultaneous observation optical system, the image reading device, the image reading method and the multidirectional simultaneous observation combined optical system of the present invention are arranged as described above to enable the faces of an object to be inspected to be simultaneously observed with accuracy and to improve the efficiency of inspection or the like. Thus, the present invention is of an extremely high industrial usage value.

The invention claimed is:

1. A multidirectional simultaneous observation optical system comprising:
  at least one of one, two or more side face imaging prism systems for obtaining side face images of at least one of one, two or more side faces of an object to be inspected;
  a bottom face imaging prism system for obtaining a bottom face image, the optical system being characterized in that each of the side face imaging prism systems has at least one of an optical path direction changing prism or an optical path direction changing prism function;
  the prism systems are provided by the side of an open space in order to obtain an image of the top face of the object to be inspected so that the open space is secured right above the object to be inspected in order that an object mount space portion is secured; and
  the prism systems are placed so that the optical paths for light exiting the prism systems extend upward above the object to be inspected, or along the same direction in parallel with each other, and so that the optical path is not obstructed; and
  characterized in that each of the side face imaging prism systems and the bottom face imaging prism system is provided with at least one of an optical path length correcting prism or an optical path length correcting prism function above the optical path direction changing prism or the optical path direction changing prism function, the at least one of the optical path length correcting prism or the optical path length correcting prism function being provided for the purpose of equalizing the working distance of the faces of the object to be inspected other than the top face of the same to the working distance of the top face.

2. A multidirectional simultaneous observation combined optical system characterized by using the two or more multidirectional simultaneous observation optical systems according to claim 1, and characterized in that multidirectional simultaneous observation of an object to be inspected can be performed by means of the multidirectional simultaneous observation optical systems.

3. The multidirectional simultaneous observation optical system according to claim 1, characterized in that each of the side face imaging prism systems and the bottom face imaging prism system is provided with an optical path length correcting prism or an optical path length correcting prism function above the optical path direction changing prism or the optical path direction changing prism function, the optical path length correcting prism or the optical path length correcting prism function being provided for the purpose of equalizing the working distance of the faces of the object to be inspected other than the top face of the same to the working distance of the top face.

4. The multidirectional simultaneous observation optical system according to claim 1, characterized in that the optical path length correcting prism or the optical path length correcting prism function is formed so as to be interchangeable or optical path length adjustable in order to make optical path length correction according to the shape and size of the object to be inspected.

5. The multidirectional simultaneous observation optical system according to claim 1, characterized in that a 45° mirror prism or a prism having a 45° mirror prism function is used as the optical path direction changing prism or the optical path direction changing prism function in the side face imaging prism system, and a trapezoidal prism or a triangular prism capable of changing the direction two times or a prism having the corresponding function is used as the optical path direction changing prism or the optical path direction changing prism function in the bottom face imaging prism system.

6. The multidirectional simultaneous observation optical system according to claim 1, characterized in that a penta prism capable of obtaining an erect image or a prism having the corresponding function is used as the optical path direction changing prism or the optical path direction changing prism function in the side face imaging prism system.

7. The multidirectional simultaneous observation optical system according to claim 1, characterized in that an optical path shifting prism or an optical path shifting prism function for shifting the optical path is provided above the optical path direction changing prism in each prism system.

8. The multidirectional simultaneous observation optical system according to claim 7, characterized in that the optical path shifting prism or the optical path shifting prism function is formed so as to reduce the optical path section for optical output from the corresponding face of the object to be inspected, in order to improve the resolution by reducing the area of light incident on a lens or the like.

9. The multidirectional simultaneous observation optical system according to claim 1, characterized by having object carrying means on which two or more objects to be inspected are mounted and which can carry and move the objects to be inspected via the object mount space portion, and characterized in that each prism system is placed so that a path for the object carrying means is secured.

10. The multidirectional simultaneous observation optical system according to claim 1, characterized in that the four side face imaging prism systems are provided and image information on the object to be inspected can be obtained as light in six directions including the direction from the top face from which an optical output can be obtained without each prism system.

11. The multidirectional simultaneous observation optical system according to claim 10, characterized in that two pairs of side face imaging prism systems opposed to each other with the object mount space portion interposed therebetween are placed as the four side face imaging prism systems orthogonally to each other or at any angle from each other.

12. The multidirectional simultaneous observation optical system according to claim 1, characterized by further including a lens facing along the optical output direction of the side face imaging prism system and the bottom face imaging prism system or a telecentric lens capable of forming a telecentric system on the side of the object to be inspected.

13. The multidirectional simultaneous observation optical system according to claim 12, characterized in that the lens has a depth of field sufficient for simultaneously adjusting in-focus planes for the faces even with respect to a complicated object to be inspected having a spherical or hyperpolyhedral shape or the like.

14. An image reading device characterized by having the multidirectional simultaneous observation optical system according to claim 11, and an electronic image pickup device including a CCD, a CMOS or a line CCD for performing photoelectric conversion processing on light obtained through the lens, and characterized in that the image reading device can be used for image analysis including image measurement.

15. An image reading method characterized by obtaining image information in the form of light on the faces of an object to be inspected by means of the multidirectional simultaneous observation optical system according to claim 11, obtaining electrically processible image information by performing photoelectric conversion processing on light obtained through the lens, by means of an electronic image pickup device including a CCD, a CMOS or a line CCD, and using the image information for image analysis including image measurement.

16. The multidirectional simultaneous observation optical system according to claim 1, characterized in that the open space is formed above the optical path direction changing prism or the optical path direction changing prism function in each of the side face imaging prism system and the bottom face imaging prism system to enable visual observation with the human eye to be easily performed.

17. The multidirectional simultaneous observation optical system according to claim 16, characterized in that a triangular mirror prism or a prism having a triangular mirror prism function is used as the optical path direction changing prism or the optical path direction changing prism function in the side face imaging prism system, and a trapezoidal prism or a triangular prism capable of changing the direction two times or a prism having the corresponding function is used as the optical path direction changing prism or the optical path direction changing prism function in the bottom face imaging prism system.

18. The multidirectional simultaneous observation optical system according to claim 16, characterized in that a pentagonal prism capable of obtaining an erect image or a prism having the corresponding function is used as the optical path direction changing prism or the optical path direction changing prism function in the side face imaging prism system.

19. The multidirectional simultaneous observation optical system according to claim 16, characterized in that an antireflection prism or an antireflection prism function is provided above the trapezoidal prism, the triangular prism or the corresponding function.

20. The multidirectional simultaneous observation optical system according to claim 16, characterized by having object carrying means on which two or more objects to be inspected are mounted and which can carry and move the objects to be inspected via the object mount space portion, and characterized in that each prism system is placed so that a path for the object carrying means is secured.

21. The multidirectional simultaneous observation optical system according to claim 16, characterized in that the four side face imaging prism systems are provided and image information on the object to be inspected can be obtained as light in six directions including the direction from the top face from which an optical output can be obtained without the prism system.

22. The multidirectional simultaneous observation optical system according to claim 21, characterized in that two pairs of side face imaging prism systems opposed to each other with the object mount space portion interposed therebetween are placed as the four side face imaging prism systems orthogonally to each other or at any angle from each other.

* * * * *